United States Patent [19]
Akhavan-Tafti et al.

[11] Patent Number: 5,523,212
[45] Date of Patent: * Jun. 4, 1996

[54] ARYL N-ALKYLACRIDANTHIOCARBOXYLATE DERIVATIVES USEFUL FOR CHEMILUMINESCENT DETECTION

[75] Inventors: Hashem Akhavan-Tafti, Sterling Heights; Renuka DeSilva, Northville; Zahra Arghavani, Sterling Heights, all of Mich.

[73] Assignee: Lumigen, Inc., Southfield, Mich.

[ * ] Notice: The portion of the term of this patent subsequent to Mar. 2, 2014, has been disclaimed.

[21] Appl. No.: 228,290

[22] Filed: Apr. 15, 1994

Related U.S. Application Data

[63] Continuation-in-part of Ser. No. 61,810, May 17, 1993, Pat. No. 5,491,072.

[51] Int. Cl.⁶ .............................. C12Q 1/28; C12Q 1/26; C12Q 1/00; C07H 5/04
[52] U.S. Cl. .................. 435/28; 435/25; 435/4; 435/19; 435/18; 435/21; 435/810; 435/968; 436/501; 436/172; 546/102; 546/108; 536/18.7
[58] Field of Search .................. 435/28, 19, 21, 435/810, 968, 25, 18, 4; 436/172, 501; 514/297; 546/102, 108; 536/18.7

[56] References Cited

U.S. PATENT DOCUMENTS

| | | | |
|---|---|---|---|
| 3,917,603 | 11/1975 | Gosteli | 546/102 |
| 3,962,252 | 6/1976 | Wu et al. | 546/102 |
| 4,687,747 | 8/1987 | Lin | 546/108 |
| 4,745,181 | 5/1988 | Law et al. | 536/18.7 |
| 4,918,192 | 4/1990 | Law et al. | 546/102 |
| 4,927,769 | 5/1990 | Chang | 435/28 |
| 4,946,958 | 8/1990 | Campbell et al. | 546/102 |
| 5,110,932 | 5/1992 | Law et al. | 546/102 |
| 5,132,204 | 7/1992 | Urdea et al. | 435/28 |
| 5,145,772 | 9/1992 | Voyta | 435/28 |
| 5,171,668 | 2/1992 | Sugiyama | 435/28 |
| 5,206,149 | 4/1993 | Oyama | 435/28 |
| 5,283,334 | 2/1994 | McCapra | 436/501 |
| 5,284,951 | 2/1994 | McCapra | 436/501 |
| 5,284,952 | 2/1994 | Ramakrishnan | 435/28 |

FOREIGN PATENT DOCUMENTS 9316195 2/1993 WIPO .

OTHER PUBLICATIONS

Steenken, S., Photochem. Photobiol., 11, 279–283 (1970).
Hapiot, P., et al., J. Am. Chem. Soc., 112(4), 1337–43 (1990).
Koper, N. W., et al., Recl. Trav. Chim. Pays–Bas, 104 (11), 296–302 (1985).
Sinha, A., et al. J. Am. Chem. Soc., 106(23), 7291–2 (1984).
Colter, A. K., et al., Can J. Chem., 62(9), 1780–4 (1984).
Chupakhin, I. M., et al., Dokl. Akad. Nauk SSSR, 250(4), 875–7 (1980).
Knappe W. R., J. Pharm. Sci., 67(3), 318–20 (1978).
Digenis, G. A., et al., J. Pharm. Sci., 65(2) 247–51 (1976).
McCapra, F., et al., in Chemiluminescence and Bioluminescence, Plenum Press, New York, 1973, pp. 313–321.
McCapra, R., Prog. Org. Chem., 8, 231–277 (1971).
McCapra, F., Pure Appl. Chem., 24, 611–629 (1970).
Kinkel, T., et al., J. Biolumin. Chemilumin. 4, 136–139 (1989).
Zomer, G., et al., Anal. Chim. Acta, 227, 11–19 (1989).
Law, S.–J., et al., J. Biolumin. Chemilumin., 4, 88–98 (1989).
Ii, M., et al., Biochem. Biophys. Res. Comm., 193(2), 540–5 (1993).
Thorpe, G., et al in Bioluminescence and Chemiluminescence, New Perspectives, J. Scholmerich, et al., Eds., pp. 199–208 (1987).
Lundin, A., et al., in Bioluminescence and Chemiluminescence, New Perspectives, J. Scholmerich, et al., Eds., pp. 555–558 (1987).
Vlasenko, S., et al., J. Biolumin. Chemilumin. 4, 164–176 (1989).
Thorpe, G. H., et al., Clin. Chem., 31, 1335 (1985).
Matthews, J. A., et al, Anal. Biochem., 151,205 (1985).
Walsh, P., et al., Nuc. Acids Res. 20,(19) 5061–5065 (1992).
McCapra Accts. Chem. Res., 9(6), 201–8 (1976).
Krick, L. J., et al., Arch. Biochem. Biophys., 217, 674 (1983).
Goto, T., et al., Tetrahedron. Lett., 4299 (1969).
Sasamoto, K., et al., Chem. Pharm. Bull, 39(2) 411–6 (1991).
Zomer, G., et al., in Luminescence Techniques in Chemical and Biochemical Analysis, W. Baeyens, et al eds., Dekker, N.Y., 505–521 (1991).
Stolle, R., J. Prakt. Chem., 105, 137 (1922).
Laemmli, U.K., Nature (London), 227, 680 (1970).
Kaltenbach et al, Chem Abstract 118(2):15573t (1993).
Kinkel et al, Jour. Bioluminescence & Chemiluminescence, vol. 4, pp. 136–139 (1989).

*Primary Examiner*—Douglas W. Robinson
*Assistant Examiner*—Louise N. Leary
*Attorney, Agent, or Firm*—Ian C. McLeod

[57] ABSTRACT

Aryl N-alkylacridanthiocarboxylate compounds which produce chemiluminescence. The compounds produce light with peroxide and peroxidase. The compounds are used as a substrate in assays for various analytes.

66 Claims, 14 Drawing Sheets

FIG.10A

```
Bacillus thuringiensis toxins 29  31          41          51          61          71          81          91         100
4.5 gene    IE TGYTPIDISL SLTQFLLSEF VPGAGFVLGL VDIIWGIFGP SQWDAFPVQI EQLINQRIEE FARNQAISRL
            29
5.3 gene    IE TGYTPIDISL SLTQFLLSEF VPGAGFVLGL VDIIWGIFGP SQWDAFLVQI EQLINQRIEE FARNQAISRL
            29
6.6 gene    IE TGYTPIDISL SLTQFLLSEF VPGAGFVLGL VDIIWGIFGP SQWDAFLVQI EQLINQRIEE FARNQAISRL 101         111         121         131         141         151         161         170
4.5 gene   EGLSNLYQIY AESFREWEAD PTNPALREEM RIQFNDMNSA LTTAIPLLAV QNYQVPLLSV YVQAANLHLS
5.3 gene   EGLSNLYQIY AESFREWEAD PTNPALREEM RIQFNDMNSA LTTAIPLFAV QNYQVPLLSV YVQAANLHLS
6.6 gene   EGLSNLYQIY AESFREWEAD PTNPALREEM RIQFNDMNSA LTTAIPLFAV QNYQVPLLSV YVQAANLHLS 171         181         191         201         211         221         231         240
4.5 gene   VLRDVSVFGQ RWGFDAATIN SRYNDLTRLI GNYTDYAVRW YNTGLERVWG PDSRDWIRYN QFRRELTLTV
5.3 gene   VLRDVSVFGQ RWGFDAATIN SRYNDLTRLI GNYTDHAVRW YNTGLERVWG PDSRDWVRYN QFRRELTLTV
6.6 gene   VLRDVSVFGQ RWGFDAATIN SRYNDLTRLI GNYTDYAVRW YNTGLERVWG PDSRDWVRYN QFRRELTLTV 241         251         261         271         281         291         301         310
4.5 gene   LDIVSLFSNY DSRRYPIRTV SQLTREIYTN PVLENFDGSF RGMAQRIEQN IRQPHLMDIL NSITIYTDVH
5.3 gene   LDIVALFPNY DSRTYPIRTV SQLTREIYTN PVLENFDGSF RGSAQGIEGS IRSPHLMDIL NSITIYTDAH
6.6 gene   LDIVALFPNY DSRRYPIRTV SQLTREIYTN PVLENFDGSF RGSAQGIERS IRSPHLMDIL NSITIYTDAH 311         321         331         341         351         360         370         380
4.5 gene   RGENYWSGHQ ITASPVGFSG PEFAFPLFGN AGNAAPPVLV SLT-GLGIFR TLSSPLYRRI ILGSGPNNQEL
           361                                                                              380
5.3 gene   RGFYYWSGHQ IMASPVGFSG PEFTFPLYGT MGNAAPQQRI VAQLGQGVYR TLSSTLYRRP FNI-GINNQQL
           361                                                                              380
6.6 gene   RGYYYWSGHQ IMASPVGFSG PEFTFPLYGT MGNAAPQQRI VAQLGQGVYR TLSSTLYRRP FNI-GINNQQL
```

```
                381                392            402            412            422            432            441        449
4.5 gene        FVLDGTEFSFASLTTNLPSTI YRQRGTVDSL DVIPPQDNSV PPRAGFSHRL SHVTML-SQA AGA-VYTLRA
                381                391            401            411            421            431            441        450
5.3 gene        SVLDGTEFAY GTSSNLPSAV YRKSGTVDSL DEIPPQNNNV PPRQGFSHRL SHVSMFRSGF SNSSVSIIRA
                381                391            401            411            421            431            441        450
6.6 gene        SVLDGTEFAY GTSSNLPSAV YRKSGTVDSL DEIPPQNNNV PPRQGFSHRL SHVSMFRSGF SNSSVSIIRA 450                460            470            480            490            500            510        519
4.5 gene        PTFSWQHRSA EFNNIIPSSQ ITQIPLTKST NLGSGTSVVK GPGFTGGDIL RRTSPGQIST LRVNITAPLS
                451                461            471            481            491            501            511        520
5.3 gene        PMFSWIHRSA EFNNIIPSSQ ITQIPLTKST NLGSGTSVVK GPGFTGGDIL RRTSPGQIST LRVNITAPLS
                451                461            471            481            491            500            510        520
6.6 gene        PMFSWIHRSA EFNNIIASDS ITQIPAVKGN FLFNG-SVIS GPGFTGGDLV RLNSSGNNIQ NRGYIEVPIHF 520                530            540            550            560            570            579
4.5 gene        QRYRVRIRYA STTNLQFHTS IDGRPINQGN FSATM              SSGSN LQSGSFRTVG FTTPFNFSNG
                521                531            541            551            561            571            580
5.3 gene        QRYRVRIRYA STTNLQFHTS IHGRPINQGN FSATM              SSGSN LQSGSFRTVG FTTPFNFSNG
                521                535            540            551            565            571            580
6.6 gene        PSTSTRYRVRVRYA SVTPI HLNVNWGNSSI FSNTVPATATSLDN LQSSDF      GYFESANAFT 580                590            600            610            620
4.5 gene        SSVFTLSAHV FNSGNEVYID RIEFVPAEVT FEAEYDLERA QK 621
                581                591            601            611            621
5.3 gene        SSVFTLSAHV FNLGNEVYID RIEFVPAKVT FEAEYDLERA QK 622
                581                592            602            612            622
6.6 gene        SSLGNIVGVRN FSGTAGVIID RFEFIPVTAT LEAEYNLERA QK 623
```

ARYL N-ALKYLACRIDANTHIOCARBOXYLATE DERIVATIVES USEFUL FOR CHEMILUMINESCENT DETECTION

CROSS REFERENCE TO RELATED APPLICATION

This application is a continuation-in-part of applicant's application Ser. No. 08/061,810 filed on May 17, 1993 now U.S. Pat. No. 5,491,072.

BACKGROUND OF THE INVENTION

(1) FIELD OF THE INVENTION

This invention relates to chemiluminescent N-alkylacridanthiocarboxylate derivatives which allow the production of light (chemiluminescence) from the acridan by reaction with a peroxide and a peroxidase. This invention relates to an improved method of generating light chemically (chemiluminescence) by the action of a peroxidase enzyme and an oxidant such as hydrogen peroxide with a group of aryl N-alkylacridancarboxylate thioesters. The invention also relates to an improved method of enhancing the amount of chemiluminescence produced from this process by the use of specific substances. The invention also relates to the use of this method to detect the peroxidase enzyme. The invention also relates to the use of this method to detect hydrogen peroxide. Further, the invention relates to the use of the method to detect and quantitate various biological molecules. For example, the method may be used to detect haptens, antigens and antibodies by the technique of immunoassay, proteins by Western blotting, DNA and RNA by Southern and Northern blotting, respectively. The method may also be used to detect DNA in DNA sequencing applications. The method may additionally be used to detect enzymes which generate hydrogen peroxide such as glucose oxidase, glucose-6-phosphate dehydrogenase, galactose oxidase and the like as are generally known in the art.

(2) DESCRIPTION OF RELATED ART

The detection and quantitation of biological molecules has been accomplished historically with excellent sensitivity by the use of radiolabeled reporter molecules. Recently numerous non-radioactive methods have been developed to avoid the hazards and inconvenience posed by these materials. Methods based on enzyme-linked analytes offer the best sensitivity since the ability to catalytically turn over substrate to produce a detectable change achieves an amplification. Substrates which generate color, fluorescence or chemiluminescence have been developed, the latter achieving the best sensitivity.

Further increases in assay sensitivity will expand the range of utility of chemiluminescence-based methods by permitting the detection of analytes present in smaller quantities or reducing the amount of time and/or reagents required to perform the assay. A way to increase the speed and sensitivity of detection in an enzymatic chemiluminescent assay is through the use of substrates which generate light with a higher efficiency or for a greater length of time.

Among the enzymes used in enzyme-linked detection methods such as immunoassays, detection of oligonucleotides and nucleic acid hybridization techniques, the most extensively used to date has been horseradish peroxidase. Chemiluminescent reagents known in the art do not permit full advantage to be taken of the beneficial properties of this enzyme in analysis mainly due to sensitivity limitations. A reagent which permits the detection of lower amounts of enzyme is needed to enable the use of peroxidase conjugates in applications requiring ultrasensitive detection. Specifically, reagents are required which generate higher levels of chemiluminescence without an accompanying increase in the background or non-specific chemiluminescence. The increased chemiluminescence may be accomplished via either a higher maximum intensity or a longer duration than compounds known in the art.

a. Oxidation of acridan. Oxidation of acridan by benzoyl peroxide in aqueous solution produced chemiluminescence with very low efficiency ($\phi_{CL}=3\times10^{-7}$) and a mixture of products including acridine (S. Steenken, Photochem. Photobiol., 11, 279–283 (1970)). N-Methylacridan is oxidized electrochemically to N-methylacridinium ion (P. Hapiot, J. Moiroux, J. M. Saveant, J. Am. Chem. Soc., 112(4), 1337–43 (1990); N. W. Koper, S. A. Jonker, J. W. Verhoeven, Recl. Trav. Chim. Pays-Bas, 104(11), 296–302 (1985)). Chemical oxidation of N-alkylacridan compounds has been performed with ferricyanide ion (A. Sinha, T. C. Bruice, J. Am. Chem. Soc., 106(23), 7291–2 (1984)), certain quinones (A. K. Colter, P. Plank, J. P. Bergsma, R. Lahti, A. A. Quesnel, A. G. Parsons, Can. J. Chem., 62(9), 1780–4 (1984)) and lithium nitrite (O. N. Chupakhin, I. M. Sosonkin, A. I. Matern, G. N. Strogov, Dokl. Akad. Nauk SSSR, 250(4), 875–7 (1980)). Oxidation of an N-alkylacridan derivative has been performed photochemically with or without a flavin compound as co-oxidant (W. R. Knappe, J. Pharm. Sci., 67(3), 318–20 (1978); G. A. Digenis, S. Shakshir, M. A. Miyamoto, H. B. Kostenbauer, J. Pharm. Sci., 65(2), 247–51 (1976)).

Aryl and alkyl esters of 10-methylacridan-9-carboxylic acid undergo autoxidation to N-methylacridone in dipolar aprotic solvents under strongly basic conditions to produce chemiluminescence (F. McCapra, Accts. Chem. Res., 9(6), 201–8 (1976); F. McCapra, M. Roth, D. Hysert, K. A. Zaklika in Chemiluminescence and Bioluminescence, Plenum Press, New York, 1973, pp. 313–321; F. McCapra, Prog. Org. Chem., 8, 231–277 (1971); F. McCapra, Pure Appl. Chem., 24, 611–629 (1970); U. S. Pat. Nos. 5,283,334 and 5,284,951 to McCapra and 5,284,952 to Ramakrishnan). Chemiluminescence quantum yields ranged from $10^{-5}$ to 0.1 and were found to increase as the $pK_a$ of the phenol or alcohol leaving group decreased. Quantum yields in aqueous solution were significantly lower due a competing non-luminescent decomposition of an intermediate. Addition of the cationic surfactant CTAB increased the apparent light yield 130-fold by preventing a competing dark reaction.

Applicants co-pending applications Ser. No. 08/061,810, filed May 17, 1993 and 08/205,093, filed Mar. 2, 1994 disclose the first use of an enzyme to oxidize substituted and unsubstituted N-alkylacridancarboxylic acid derivatives to generate chemiluminescence. In the presence of a peroxidase enzyme and a peroxide, N-alkylacridancarboxylic acid derivatives are efficiently oxidized to produce the N-alkylacridone and blue chemiluminescence.

b. *Chemiluminescent oxidation of acridinium esters.* The chemiluminescent oxidation of aliphatic and aromatic esters of N-alkylacridinium carboxylic acid by $H_2O_2$ in alkaline solution is a well known reaction. The high chemiluminescence quantum yield approaching 0.1 has led to development of derivatives with pendant reactive groups for attachment to biological molecules. Numerous chemiluminescent immunoassays and oligonucleotide probe assays utilizing acridinium ester labels have been reported, and are particularly described in U.S. Pat. Nos. 5,284,951 and 5,284,952, cited above.

The use of acridinium esters (AE's), especially when labeled to a protein or oligonucleotide suffers from two disadvantages. The chief problem is limited hydrolytic stability. Acridinium ester conjugates decompose steadily at or slightly above room temperature. Depending on the substitution of the leaving group storage at $-20\,°$ C. may be required for extended storage.

A second disadvantage of acridinium esters is the tendency to add nucleophiles such as water at the 9-position to spontaneously form a pseudo-base intermediate which is non-luminescent and decomposes in a pH-dependent manner in a dark process. In practice the pH of solutions containing acridinium esters must be first lowered to reverse pseudo-base formation and then raised in the presence of $H_2O_2$ to produce light.

Amides, thioesters and sulfonamides of N-alkylacridinium carboxylic acid have been shown to emit light when oxidized under these conditions (T. Kinkel, H. Lubbers, E. Schmidt, P. Molz, H. J. Skripczyk, J. Biolumin. Chemilumin., 4, 136–139, (1989), G. Zomer, J. F. C. Stavenuiter, Anal. Chim. Acta, 227, 11–19 (1989)). These modifications of the leaving group only partially improve the storage stability performance.

A more fundamental limitation to the use of acridinium esters as chemiluminescent labels lies in the fact that when used as direct labels, only up to at most about 10 molecules can be attached to a protein or oligonucleotide. Coupled with the quantum efficiency for producing a photon ($\leq 10\%$), an acridinium ester-labeled analyte can generate at most one photon of light. In contrast, enzyme-labeled analytes detected by a chemiluminescent reaction can potentially generate several orders of magnitude more light per analyte molecule detected by virtue of the catalytic action of the enzyme.

An attempt to increase the number of acridinium ester molecules associated with an analyte in an immunoassay was made by constructing an antibody-liposome conjugate wherein the liposome contained an unspecified number of acridinium esters (S. -J. Law, T. Miller, U. Piran, C. Klukas, S. Chang, J. Unger, J.. Biolumin. Chemilumin., 4, 88–98, (1989)). This method only produced a modest increase in signal over a comparable assay using directly labeled AE's.

c. *Chemiluminescent Detection of Horseradish Peroxidase.* Amino-substituted cyclic acylhydrazides such as luminol and isoluminol react with $H_2O_2$ and a peroxidase enzyme catalyst (such as horseradish peroxidase, HRP) under basic conditions with emission of light. This reaction has been used as the basis for analytical methods for the detection of $H_2O_2$ and for the peroxidase enzyme. An analog of luminol (8-amino-5-chloro-7-phenylpyrido [3,4-d]pyridazine-1, 4(2H, 3H)dione) has been used in an enhanced chemiluminescent assay with HRP (M. Ii, H. Yoshida, Y. Aramaki, H. Masuya, T. Hada, M. Terada, M. Hatanaka, Y. Ichimori, Biochem. Biophys. Res. Comm., 193(2), 540–5 (1993)). Application of this compound in an immunoassay led to a two-fold lowering of the detection limit compared to detection using luminol. Another chemiluminescent compound oxidized by a peroxidase enzyme and a peroxide is a hydroxy-substituted phthalhydrazide (Akhavan-Tafti co-pending U.S. patent application No. 965,231, filed Oct. 23, 1992). Applicant's co-pending applications Ser. No. 08/061,810 and 08/205,093 disclose chemiluminescent N-alkylacridancarboxylic acid esters and sulfonimides which produce light upon reaction with a peroxide and a peroxidase for use in detecting peroxidase enzymes and in assays.

Numerous enhancers have also been employed in conjunction with the use of luminol to increase the intensity and duration of light emitted. These include benzothiazole derivatives such as D-luciferin, various phenolic compounds such as p-iodophenol and p-phenylphenol and aromatic amines (G. Thorpe, L. Kricka, in Bioluminescence and Chemiluminescence, New Perspectives, J. Scholmerich, et al, Eds., pp. 199–208 (1987)). For the purposes of the present invention phenolic compounds are taken to mean hydroxylic aromatic compounds which will also include compounds such as 2-naphthol and 6-bromo-2-naphthol which are known to enhance other peroxidase reactions in addition to the aforementioned substituted hydroxyphenyl compounds. Other compounds which function as enhancers of the chemiluminescent oxidation of amino-substituted cyclic acylhydrazides by a peroxidase include 4-(4-hydroxyphenyl)thiazole (M. Ii, H. Yoshida, Y. Aramaki, H. Masuya, T. Hada, M. Terada, M. Hatanaka, Y. Ichimori, Biochem. Biophys. Res. Comm., 193(2), 540–5 (1993), a group of compounds disclosed in U.S. Pat. No. 5,171,668 to Sugiyama, 2-hydroxy-9-fluorenone, and a group of hydroxy-substituted benzoxazole derivatives as disclosed in U.S. Pat. No. 5,206,149 to Oyama. The mechanism of oxidation of cyclic acylhydrazides by the combination of a peroxide and a peroxidase enzyme is very complex and remains the subject of intense debate (A. Lundin, L. Hallander, in Bioluminescence and Chemiluminescence, New Perspectives, J. Scholmerich, et al, Eds., pp. 555–558 (1987); S. Vlasenko, A Arefyev, A. Klimov, B. Kim, E. Gorovits, A. Osipov, E. Gavrilova, A. Yegorov, J. Biolumin. Chemilumin. 4, 164–176 (1989)). This difficulty has hampered the development of new chemiluminescent reactions catalyzed by peroxidases.

d. *Assays using HRP.* The enzyme horseradish peroxidase has found widespread use in enzyme immunoassays and DNA hybridization assays with chemiluminescent detection using luminol or isoluminol as substrate (G. H. Thorpe, L. J. Kricka, S. B. Mosely, T. P. Whitehead, Clin. Chem., 31, 1335 (1985), J. A. Matthews, A. Batki, C. Hynds, L. J. Kricka, Anal. Biochem., 151,205, (1985), P. Walsh, J. Varlaro, R. Reynolds, Nuc. Acids Res. 20,(19) 5061–5065 (1992). Commercially available kits for conjugation of HRP with enhanced luminol chemiluminescent detection are available. Chemiluminescent assays using a peroxidase enzyme known in the art are not able to detect the lowest levels of certain analytes such as the thyroid hormone TSH, mainly due to the inability to detect the enzyme at extremely low levels. A chemiluminescent reagent which permits the detection of lower amounts of enzyme is needed for such assays.

e. *Chemiluminescence Enhancement by Surfactants.* Enhancement of chemiluminescent reactions using polymeric and monomeric surfactants is known in the art. Enhancement may occur by affecting the outcome of one or more steps e.g. by increasing the fluorescence quantum yield of the emitter, by increasing the percentage of product molecules produced in the excited state, by increasing the fraction of molecules undergoing the chemiluminescent reaction through inhibition of competing side reactions (McCapra Accts. Chem. Res., 9(6), 201–8 (1976)) or by promoting the action of an enzyme catalyst. No clear or consistent pattern exists concerning the effect of polymeric and monomeric surfactants on chemiluminescent reactions. It is impossible to predict which surfactant compounds, if any, may enhance the chemiluminescence from a particular process without substantial experimentation.

U.S. Pat. No. 5,145,772 to Voyta discloses enhancement of enzymatically generated chemiluminescence from 1,2-dioxetanes in the presence of polymeric compounds. Certain cationic polymer compounds were effective chemiluminescence enhancers; nonionic polymeric compounds were generally ineffective and the lone anionic polymer, Example 45, significantly decreased light emission.

U.S Pat. No. 4,927,769 to Chang discloses enhancement by surfactants of the chemical oxidation of acridinium esters with alkaline hydrogen peroxide. These acridinium ester compounds are different than the acridan compounds of the present invention in that reaction of the acridinium ester compounds do not involve the use of enzymes. Several of the tested surfactants (see Table 2 in Chang) provided only marginal enhancement.

A report on the effect of surfactants on the firefly luciferin-luciferase reaction (L. J. Kricka, M. DeLuca, Arch. Biochem. Biophys., 217, 674 (1983)) discloses enhancement of the light yield with nonionic surfactants by affecting the enzyme reactivity; a cationic surfactant totally extinguished light emission by inhibiting the enzyme.

A paper (T. Goto, H. Fukatsu, Tetrahedron. Lett., 4299 (1969)) teaches chemiluminescence enhancement of the chemical oxidation of Cypridina luciferin in the presence of nonionic and cationic but not anionic surfactants even though the fluorescence quantum yield of the emitter was increased in all three types of surfactants.

A paper (K. Sasamoto, Y. Ohkura, Chem. Pharm. Bull, 39(2), 411–6 (1991)) discloses enhancement by a cationic surfactant of chemiluminescence from chemical oxidation of a dialkylaminobenzofuranyl-substituted cyclic diacylhydrazide. An anionic surfactant was ineffective at enhancing the chemiluminescence, while a nonionic surfactant diminished light production.

OBJECTS

It is therefore an object of the present invention to provide an improved method and aryl N-alkylacridanthiocarboxylate derivatives with superior properties for use in generating chemiluminescence by the action of a peroxidase enzyme for the detection of biological materials and compounds. It is also an object of the present invention to provide an improved method and kit using aryl N-alkylacridanthiocarboxylate derivatives in solution or on membranes for use in generating chemiluminescence by the action of a peroxidase enzyme for the detection of peroxidase enzymes and enzyme-conjugates. Additionally, it is an object of the present invention to provide an improved method and kit using aryl N-alkylacridanthiocarboxylate derivatives for use in generating chemiluminescence by the action of a peroxidase enzyme for use in nucleic acid assays in solution and on surfaces. Further, it is an object of the present invention to provide an improved method and kit using aryl N-alkylacridan-thiocarboxylate derivatives for use in generating chemiluminescence by the action of a peroxidase enzyme for detection of proteins in Western blots and DNA in Southern blots and other DNA hybridization assays. Further, it is an object of the present invention to provide an improved method and kit using aryl N-alkylacridanthiocarboxylate derivatives for use in generating chemiluminescence by the action of a peroxidase enzyme for detection of haptens, proteins and antibodies in enzyme immunoassays.

IN THE DRAWINGS

FIG. 1 is a graph showing a comparison of the light emission profiles from a reagent containing phenyl 10-methylacridan-9-thiocarboxylate (5a) of the present invention, a reagent containing the acridan phenyl 10-methylacridan-9-carboxylate and a reagent containing the acridan ethyl 10-methylacridan-9-thiocarboxylate. Forty μL each of three formulations were reacted in separate experiments with 1 μL of a solution containing $1.4 \times 10^{-16}$ mol of HRP in water. These formulations consisted of: (1) 0.05 mM acridan compound 5a in 0.01M tris buffer, pH 8.0, 0.4 mM urea peroxide, 0.1 mM p-phenylphenol, 0.025% TWEEN 20, 1 mM EDTA; (2) an identical formulation containing phenyl 10-methylacridan-9-carboxylate in place of 5a and (3) an identical formulation containing ethyl 10-methylacridan-9-thiocarboxylate in place of 5a. The figure shows the improved generation of light emission (in Relative Light Units, RLU) using a reagent of the present invention under these conditions compared to the other reagents.

FIG. 2 is a graph showing a comparison of the light emission profiles from a reagent containing 4'-hydroxyphenyl 10-methylacridan-9-thiocarboxylate (5b) of the present invention, a reagent containing the acridan phenyl 10-methylacridan-9-carboxylate and a reagent containing the acridan ethyl 10-methylacridan-9-thiocarboxylate. Forty μL each of three formulations were reacted in separate experiments with 1 μL of a solution containing $1.4 \times 10^{-16}$ mol of HRP in water. These formulations consisted of: (1) 0.05 mM acridan compound 5b in 0.01M tris buffer, pH 8.0, 0.4 mM urea peroxide, 0.1 mM p-phenylphenol, 0.025% TWEEN 20, 1 mM EDTA; (2) an identical formulation containing phenyl 10-methylacridan-9-carboxylate in place of 5b and (3) an identical formulation containing ethyl 10-methylacridan-9-thiocarboxylate in place of 5b. FIG. 2 shows the improved generation of light emission using a reagent of the present invention under these conditions compared to the other reagents.

FIG. 3 is a graph showing a comparison of the light emission profiles from a reagent containing 4'-fluorophenyl 10-methylacridan-9-thiocarboxylate (5d) of the present invention, a reagent containing the acridan phenyl 10-methylacridan-9-carboxylate and a reagent containing the acridan ethyl 10-methylacridan-9-thiocarboxylate. Forty μL each of three formulations were reacted in separate experiments with 1 μL of a solution containing $1.4 \times 10^{-16}$ mol of HRP in water. These formulations consisted of: (1) 0.05 mM acridan compound 5d in 0.01M tris buffer, pH 8.0, 0.4 mM urea peroxide, 0.1 mM p-phenylphenol, 0.025% TWEEN 20, 1 mM EDTA; (2) an identical formulation containing phenyl 10-methylacridan-9-carboxylate in place of 5d and (3) an identical formulation containing ethyl 10-methylacridan-9-thiocarboxylate in place of 5d. FIG. 3 shows the improved generation of light emission using a reagent of the present invention under these conditions compared to the other reagents.

FIG. 4 is a graph showing a comparison of the light emission profiles from a reagent containing 4'-trifluoromethylphenyl 10-methylacridan-9-thiocarboxylate (5e) of the present invention, a reagent containing the acridan phenyl 10-methylacridan-9-carboxylate and a reagent containing the acridan ethyl 10-methylacridan-9-thiocarboxylate. Forty μL each of three formulations were reacted in separate experiments with 1 μL of a solution containing 1.4×10–16 mol of HRP in water. These formulations consisted of: (1) 0.05 mM acridan compound 5e in 0.01M tris buffer, pH 8.0, 0.4 mM urea peroxide, 0.1 mM p-phenylphenol, 0.025% TWEEN 20, 1 mM EDTA; (2) an identical formulation containing phenyl 10-methylacridan-9-carboxylate in place of 5e and (3) an identical formulation containing ethyl 10-methylacridan-9-thiocarboxylate in place of 5e. FIG. 4 shows the improved generation of light emission using a reagent of the present invention under these conditions compared to the other reagents.

FIG. 5 is a graph showing a comparison of the light emission profiles from a reagent containing 4'-methoxyphenyl 10-methylacridan-9-thiocarboxylate (5f) of the present invention, a reagent containing the acridan phenyl 10-methylacridan-9-carboxylate and a reagent containing the acridan ethyl 10-methylacridan-9-thiocarboxylate. Forty μL each of three formulations were reacted in separate experiments with 1 μL of a solution containing $1.4 \times 10^{-16}$ mol of HRP in water. These formulations consisted of: (1) 0.05 mM acridan compound 5f in 0.01M tris buffer, pH 8.0, 0.4 mM urea peroxide, 0.1 mM p-phenylphenol, 0,025% TWEEN 20, 1 mM EDTA; (2) an identical formulation containing phenyl 10-methylacridan-9-carboxylate in place of 5f and (3) an identical formulation containing ethyl 10-methylacridan-9-thiocarboxylate in place of 5f. FIG. 5 shows the improved generation of light emission using a reagent of the present invention under these conditions compared to the other reagents.

FIG. 6 is a graph showing a comparison of the light emission profiles from a reagent containing 2',6'-dichlorophenyl 10-methylacridan-9-thiocarboxylate (5g) of the present invention, a reagent containing the acridan phenyl 10-methylacridan-9-carboxylate and a reagent containing the acridan ethyl 10-methylacridan-9-thiocarboxylate. Forty μL each of three formulations were reacted in separate experiments with 1 μL of a solution containing $1.4 \times 10^{-16}$ mol of HRP in water. These formulations consisted of: (1) 0.05 mM acridan compound 5g in 0.01M tris buffer, pH 8.0, 0.4 mM urea peroxide, 0.1 mM p-phenylphenol, 0.025% TWEEN 20, 1 mM EDTA; (2) an identical formulation containing phenyl 10-methylacridan-9-carboxylate in place of 5g and (3) an identical formulation containing ethyl 10-methylacridan-9-thiocarboxylate in place of 5g. FIG. 6 shows the improved generation of light emission using a reagent of the present invention under these conditions compared to the other reagents.

FIG. 7 is a graph showing a comparison of the light emission profiles from a reagent containing 2-naphthyl 10-methylacridan-9-thiocarboxylate (5h) of the present invention, a reagent containing the acridan phenyl 10-methylacridan-9-carboxylate and a reagent containing the acridan ethyl 10-methylacridan-9-thiocarboxylate. Forty μL each of three formulations were reacted in separate experiments with 1 μL of a solution containing $1.4 \times 10^{-16}$ mol of HRP in water. These formulations consisted of: (1) 0.05 mM acridan compound 5h in 0.01M tris buffer, pH 8.0, 0.4 mM urea peroxide, 0.1 mM p-phenylphenol, 0.025% TWEEN 20, 1 mM EDTA; (2) an identical formulation containing phenyl 10-methylacridan-9-carboxylate in place of 5h and (3) an identical formulation containing ethyl 10-methylacridan-9-thiocarboxylate in place of 5h. FIG. 7 shows the improved generation of light emission using a reagent of the present invention under these conditions compared to the other reagents.

FIG. 8 is a graph showing a comparison of the light emission profiles from a reagent containing 4'-fluorophenyl 3-methoxy-10-methylacridan-9-thiocarboxylate (5j) of the present invention, a reagent containing the acridan phenyl 10-methylacridan-9-carboxylate and a reagent containing the acridan ethyl 10-methylacridan-9-thiocarboxylate. Forty μL each of three formulations were reacted in separate experiments with 1 μL of a solution containing $1.4 \times 10^{-16}$ mol of HRP in water. These formulations consisted of: (1) 0.05 mM acridan compound 5j in 0.01M tris buffer, pH 8.0, 0.4 mM urea peroxide, 0.1 mM p-phenylphenol, 0.025% TWEEN 20, 1 mM EDTA; (2) an identical formulation containing phenyl 10-methylacridan-9-carboxylate in place of 5j and (3) an identical formulation containing ethyl 10-methylacridan-9-thiocarboxylate in place of 5j. FIG. 8 shows the improved generation of light emission using a reagent of the present invention under these conditions compared to the other reagents.

FIG. 9 is a graph showing a comparison of the linearity of detection of HRP using a reagent composition of the present invention and a commercially available optimized reagent containing luminol. In separate experiments, 40 μL of a solution containing acridan 5a and a commercial reagent (Amersham ECL) were mixed at room temperature with 1 μL aliquots of HRP containing the indicated amounts of enzyme. Data from the composition containing acridan a was measured at 15 min while data from the ECL reagent represent the maximum light intensity. The term S-B refers to the chemiluminescence signal (S) in RLU in the presence of HRP corrected for background chemiluminescence (B) in the absence of HRP. The composition containing acridan 5a is capable of 100-fold greater sensitivity of detection than the ECL reagent.

FIG. 10 is a graph showing a comparison of the linearity of detection of HRP using a reagent composition of the present invention and a commercially available optimized reagent containing luminol. In separate experiments, 40 μL of a solution containing acridan 5d and a commercial reagent (Amersham ECL) were mixed at room temperature with 1 μL aliquots of HRP containing the indicated amounts of enzyme. Data from the composition containing acridan 5d was measured at 15 min while data from the ECL reagent represent the maximum light intensity. The term S-B has the same meaning as in FIG. 9. The composition containing acridan 5d is capable of 100-fold greater sensitivity of detection than the ECL reagent.

FIG. 11 is a graph showing a comparison of the linearity of detection of HRP using a reagent composition of the present invention and a commercially available optimized reagent containing luminol. In separate experiments, 40 μL of a solution containing acridan 5e and a commercial reagent (Amersham ECL) were mixed at room temperature with 1 μL aliquots of HRP containing the indicated amounts of enzyme. Data from the composition containing acridan e was measured at 15 min while data from the ECL reagent represent the maximum light intensity. The term S-B has the same meaning as in FIG. 9. The composition containing acridan 5e is capable of 100-fold greater sensitivity of detection than the ECL reagent.

FIG. 12 is a graph showing a comparison of the linearity of detection of HRP using a reagent composition of the present invention and a commercially available optimized reagent containing luminol. In separate experiments, 40 μL of a solution containing acridan 5j and a commercial reagent (Amersham ECL) were mixed at room temperature with 1 μL aliquots of HRP containing the indicated amounts of enzyme. Data from the composition containing acridan 5j was measured at 15 min while data from the ECL reagent represent the maximum light intensity. The term S-B has the same meaning as in FIG. 9. The composition containing acridan 5j is capable of 100-fold greater sensitivity of detection than the ECL reagent.

FIG. 13A, 13B and 13C shows the result of a Western blot analysis of human transferrin on PVDF with chemiluminescent detection using fractionated goat anti-human transferrin serum, rabbit anti-goat IgG-peroxidase conjugate. Human transferrin loaded into each slot was (1) 1000 pg, (2) 200 pg, (3) 50 pg, (4) 20 pg, (5) 5 pg. Chemiluminescent detection was performed using A: a commercial reagent containing luminol (ECL), B: a reagent composition containing the acridan 4'-hydroxyphenyl 10-methylacridan-9-carboxylate previously disclosed in applicant's co-pending application Ser. No. 08/061,810 and C: a reagent composition containing the acridan 5a of the present invention. The blots were exposed to X-OMAT AR X-ray film for 15 sec after a 14 minute incubation. The image has been scanned and digitally reproduced. The results show the superior image obtained with acridan 5a of the present invention.

FIG. 14 shows the result of a Southern blot analysis of EcoRI-restricted mouse genomic DNA on nylon with chemiluminescent detection using a fluorescein-labeled v-mos probe and horseradish peroxidase-anti-fluorescein conjugate, and a composition of the invention containing acridan 5a. The blot was exposed to X-OMAT AR X-ray film for 10 min after a 9 min incubation. The image has been scanned and digitally reproduced. The results show an image of the single copy gene in both tracks of the blot using the detection reagent of the present invention.

DESCRIPTION OF THE PREFERRED EMBODIMENTS

Figure 1:
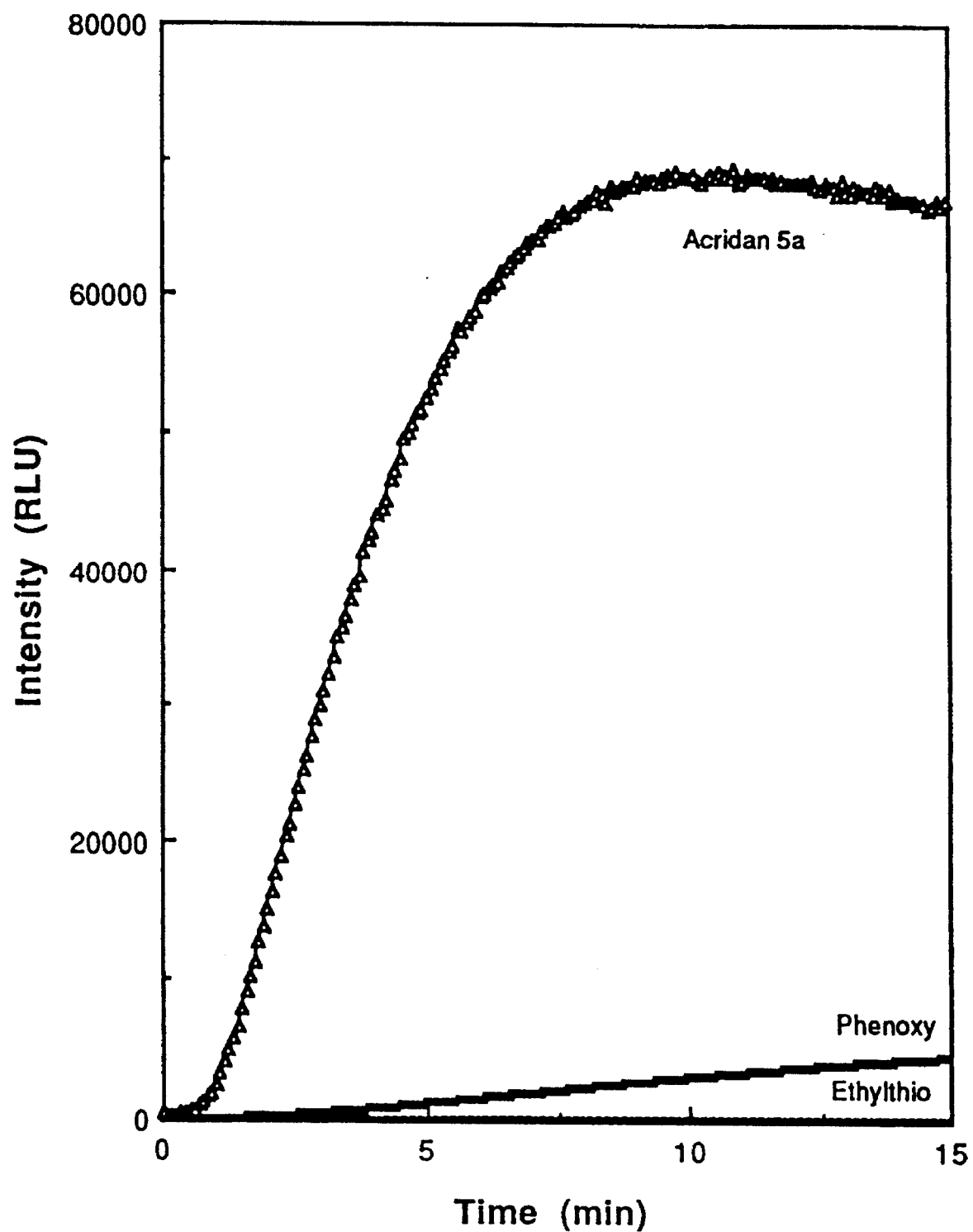
Figure 2:
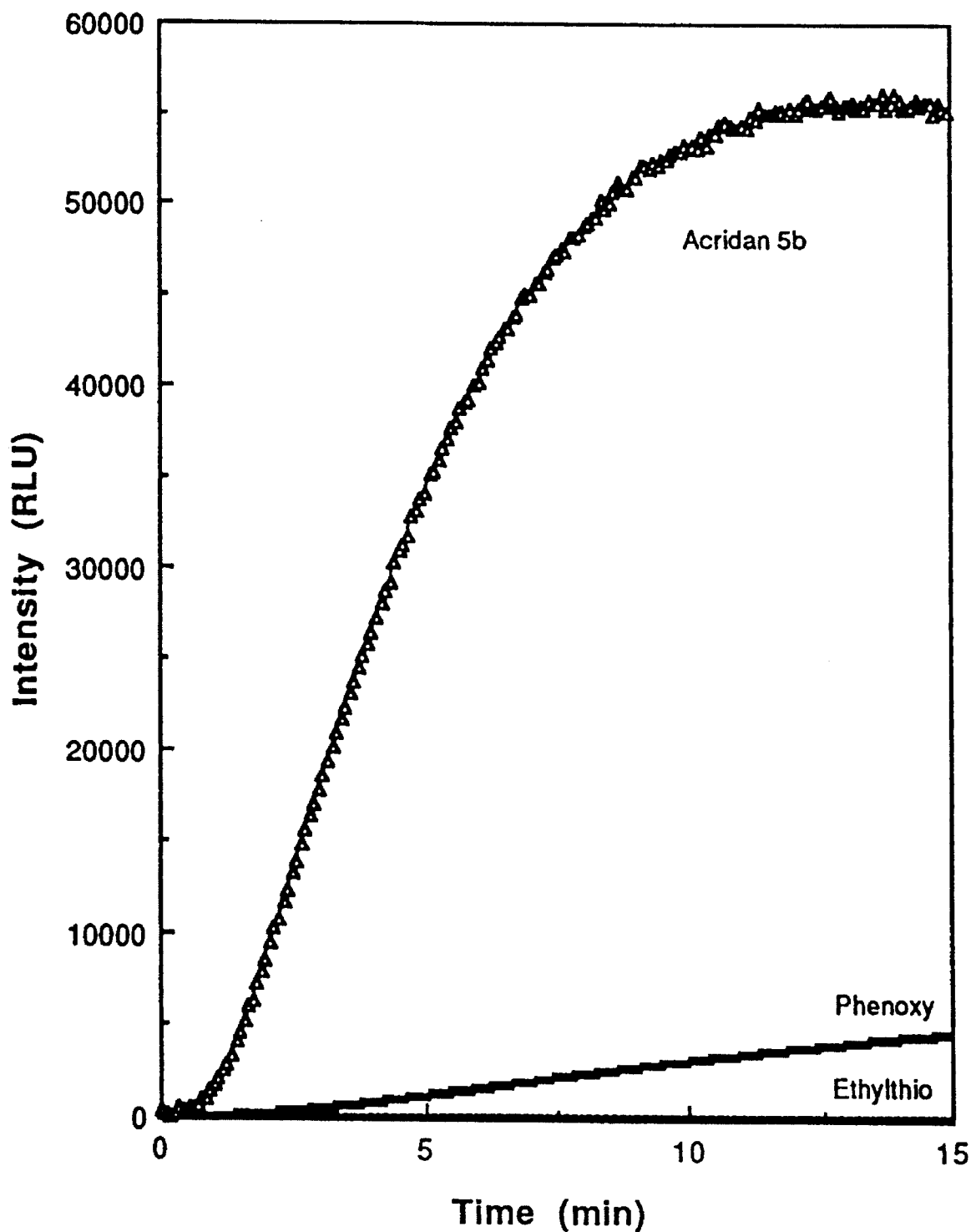
Figure 3:
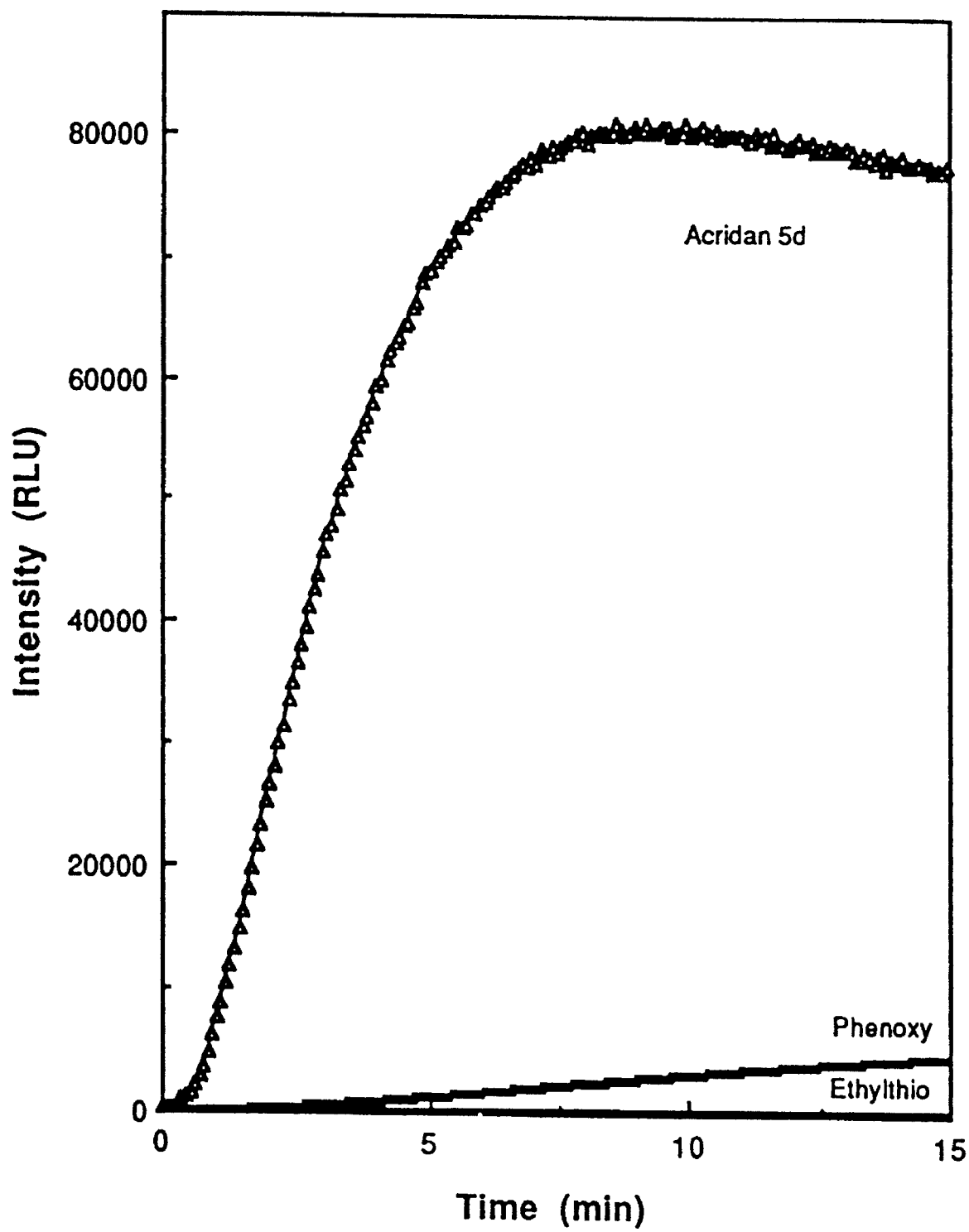
Figure 4:
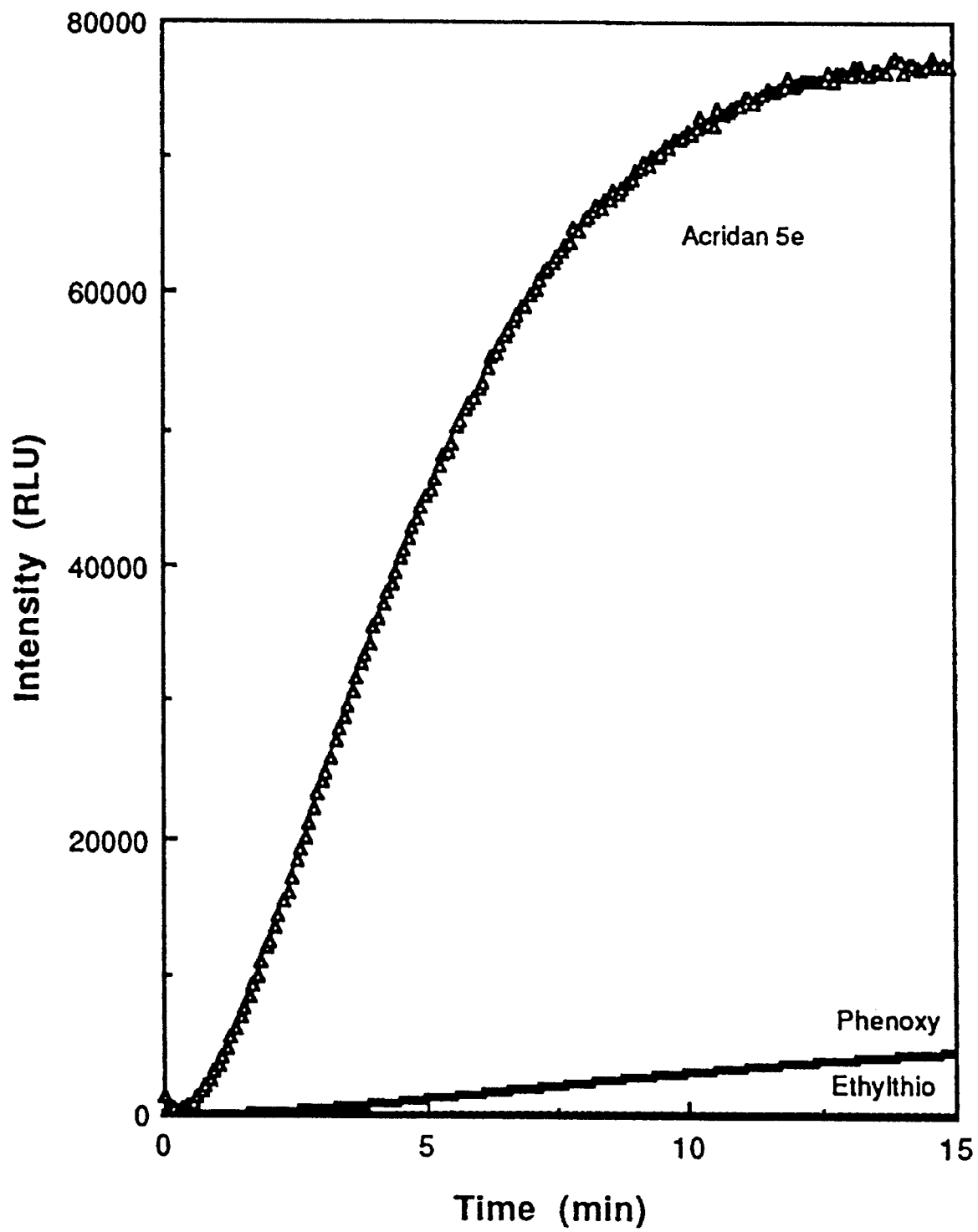
Figure 5:
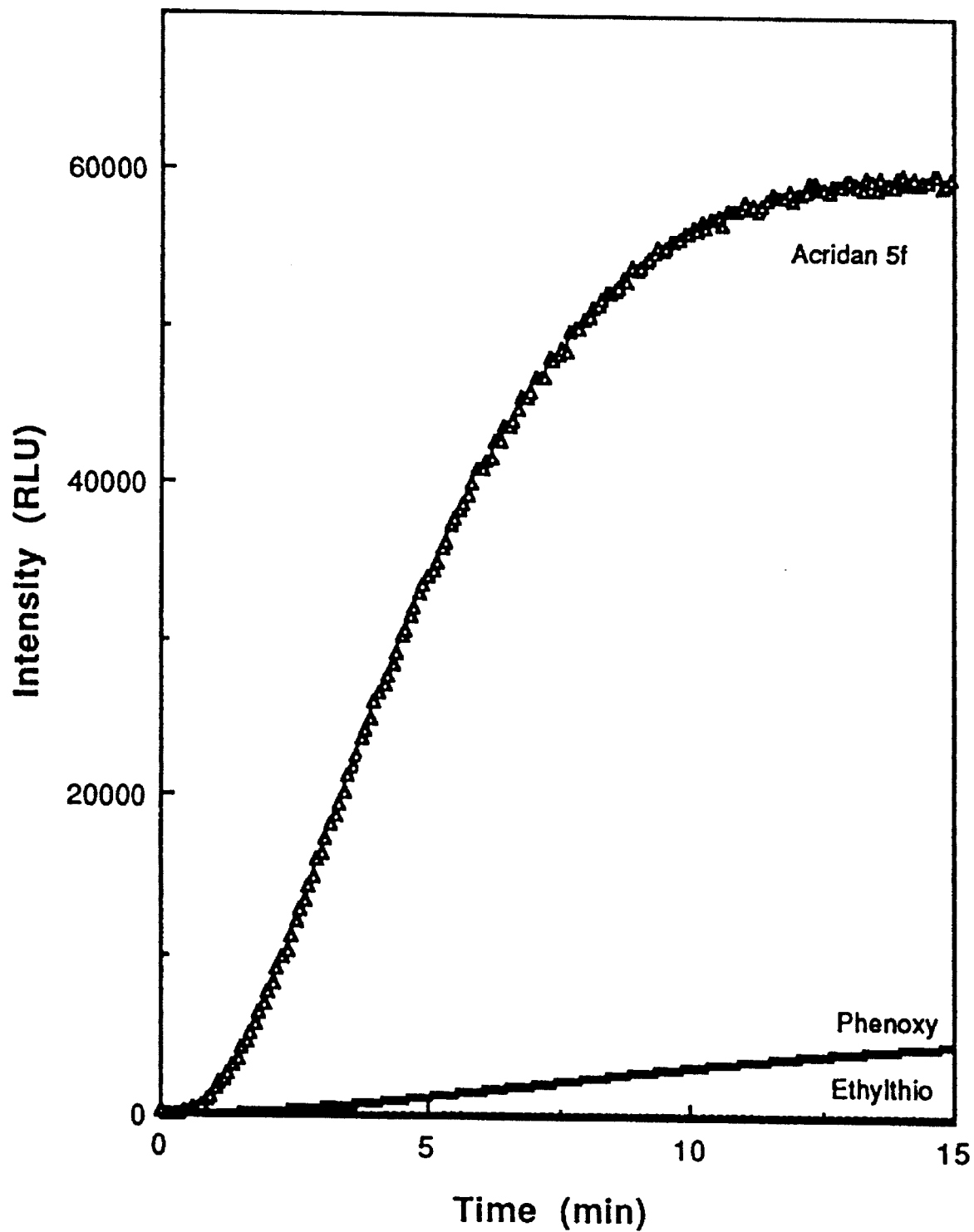
Figure 6:
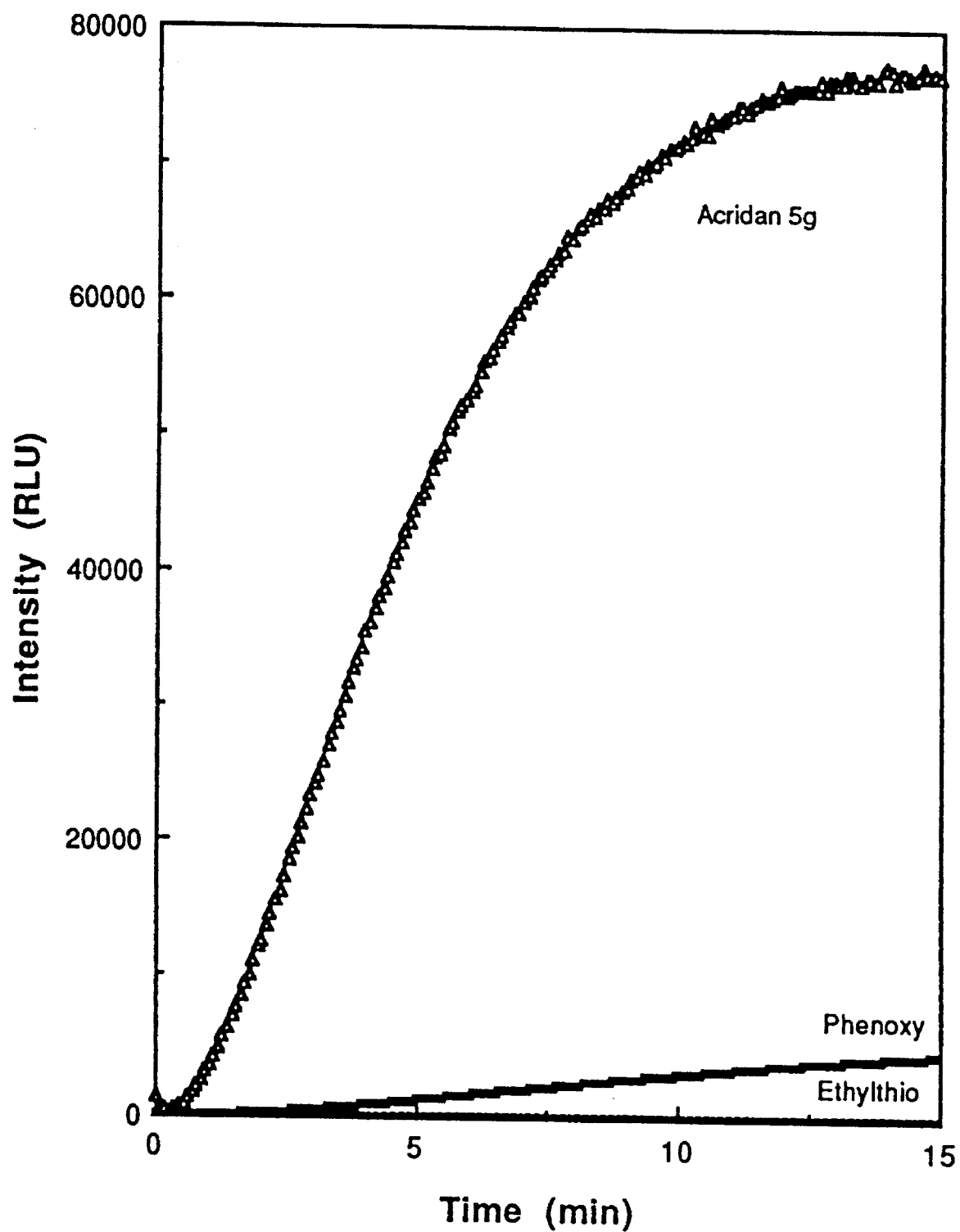
Figure 7:
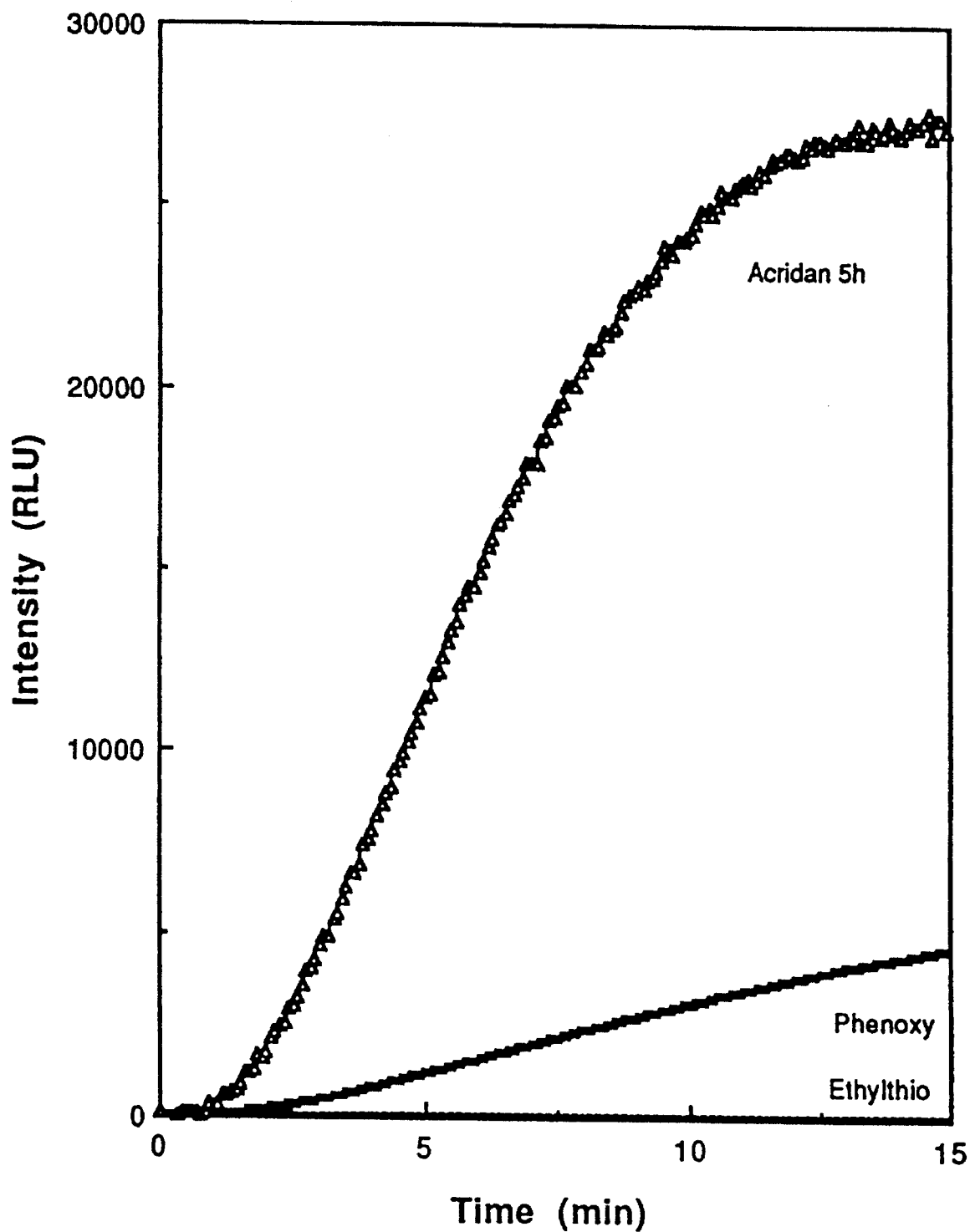
Figure 8:
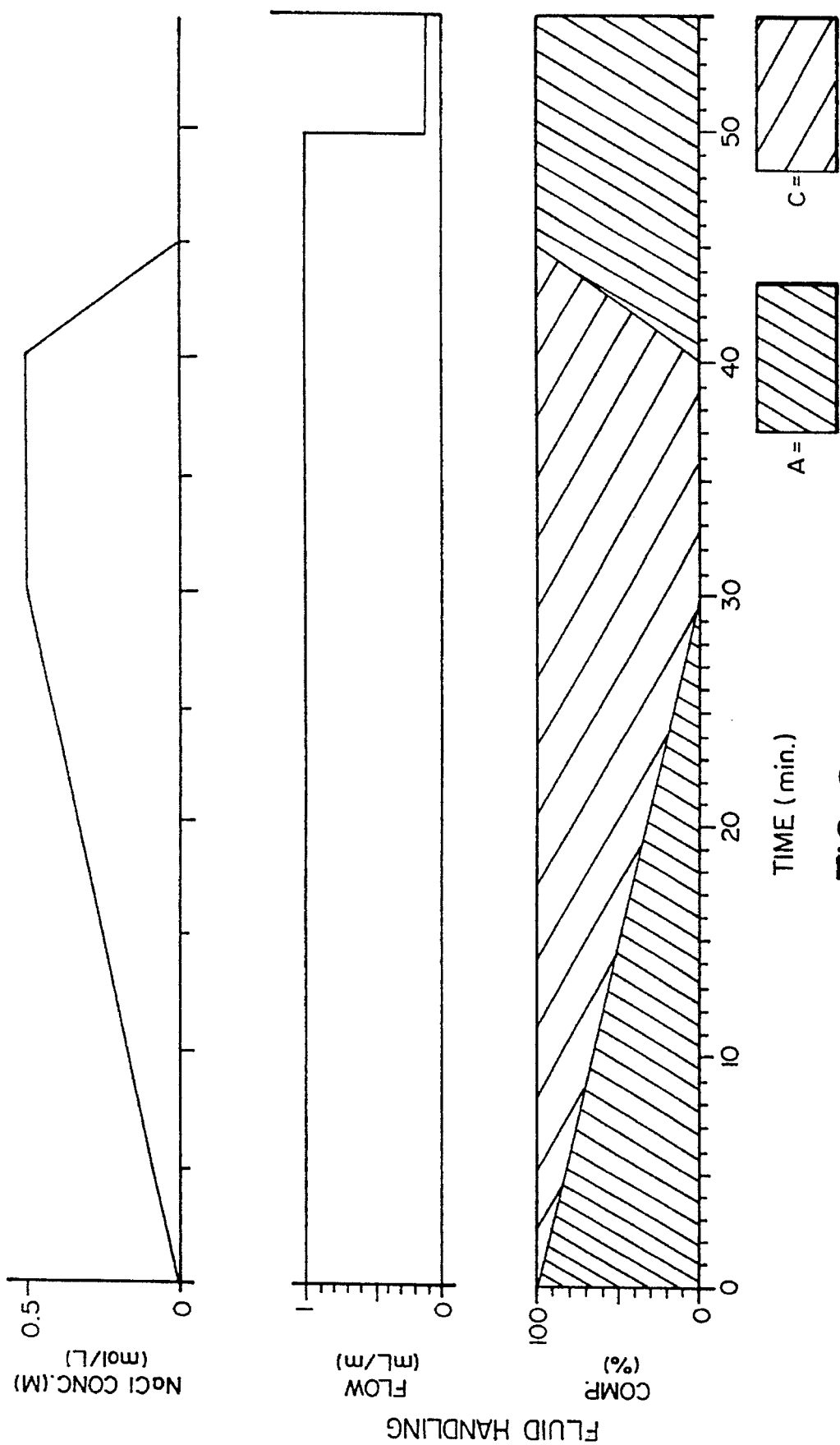
Figure 9:
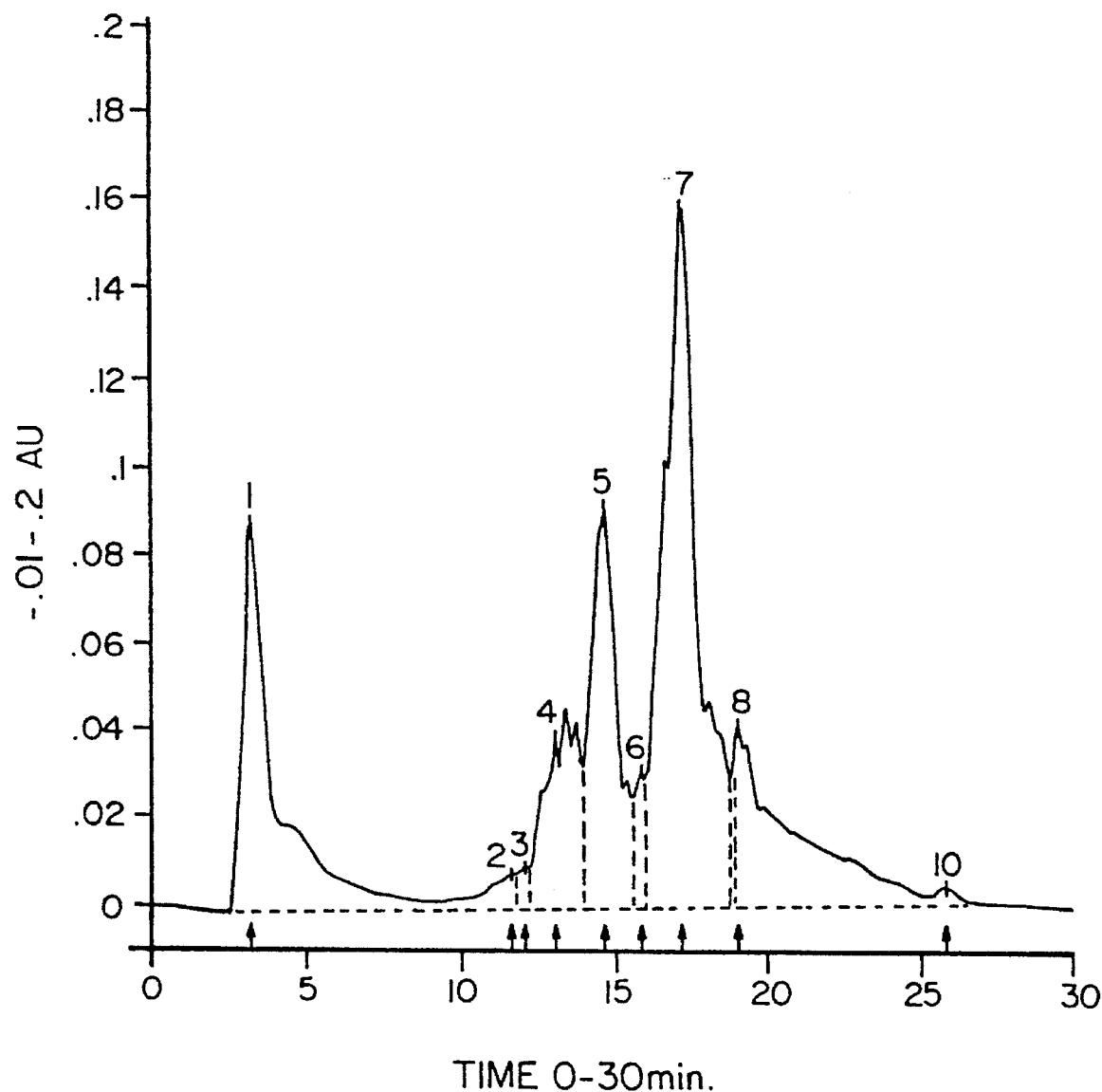
Figure 12:
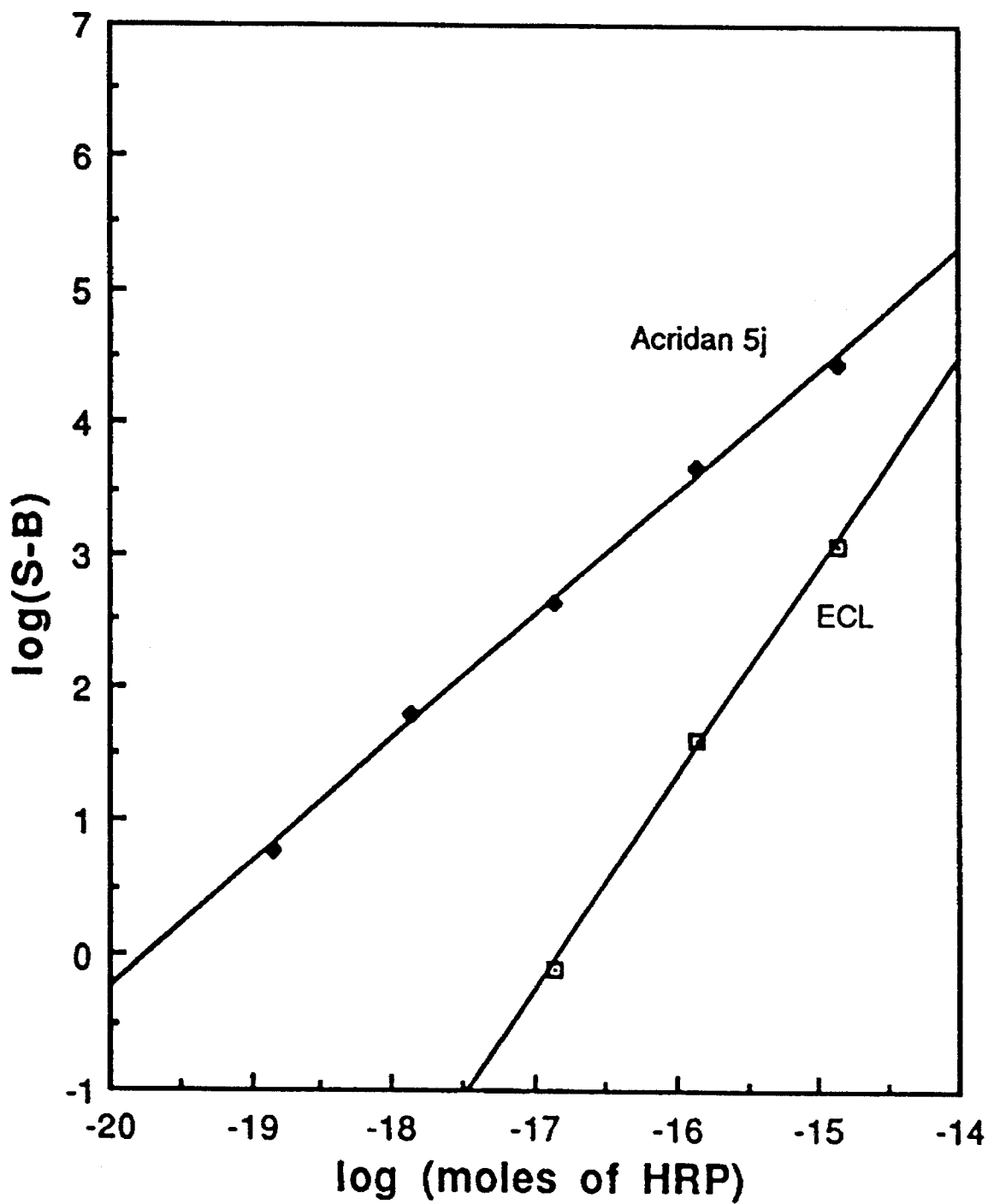
Figure 13A:
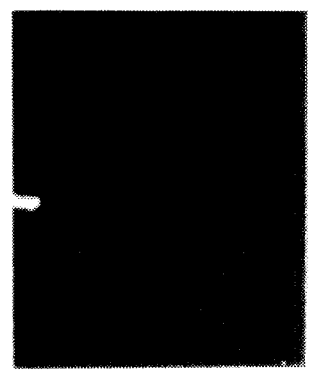
Figure 13B:
Figure 13C:
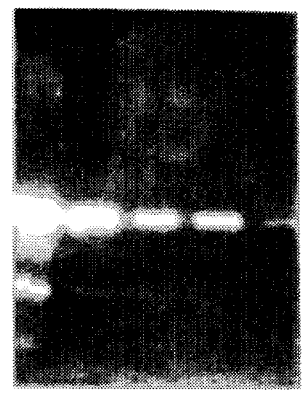

Acridans of the formula:

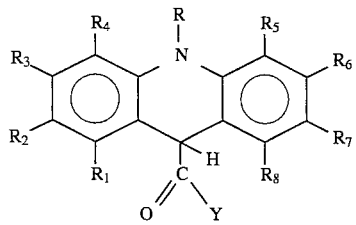
(I)

wherein R is selected from alkyl, heteroalkyl and aralkyl groups, wherein $R_1$ through $R_8$ are independently selected from hydrogen and groups which allow the production of light and wherein Y is a leaving group which allows the production of light (chemiluminescence) from the acridan by reaction with a peroxide and a peroxidase were disclosed in applicant's co-pending applications Ser. No. 061,810 and 08/205,093. It has now been discovered that certain derivatives including aryl thioester derivatives (Formula I, Y=SAr) provide superior properties in producing chemiluminescence.

The present invention relates to an improved acridan of the formula:

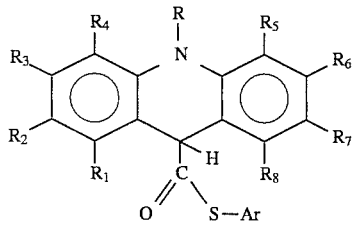
(II)

wherein R is selected from alkyl, heteroalkyl and aralkyl groups, wherein $R_1$ through $R_8$ are independently selected from hydrogen and groups which allow the production of light and wherein Ar is selected from substituted and unsubstituted aryl (particularly phenyl, naphthyl and biphenyl) and heteroaryl (particularly pyridyl, quinolyl and xanthenyl) groups which allow the production of light from the acridan by reaction with a peroxide and a peroxidase.

The present invention relates to a reagent composition which generates light in the presence of a peroxidase the improvement which comprises:

a) an acridan of the formula:

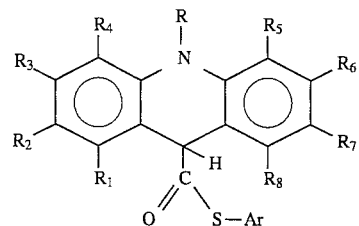

wherein R is selected from alkyl, heteroalkyl and aralkyl groups, wherein $R_1$ through $R_8$ are independently selected from groups which allow the production of light and wherein Ar is selected from substituted and unsubstituted aryl (particularly phenyl, naphthyl and biphenyl), and heteroaryl (particularly pyridyl, quinolyl and xanthenyl) groups which allow the production of light from the acridan by reaction with a peroxide and a peroxidase;

b) optionally a phenolic compound which enhances light production from the acridan;

c) a peroxide compound which participates in the reaction of the acridan with the peroxidase;

d) a chelating agent which prevents the peroxide compound from reacting prior to addition of the peroxidase to the composition; and e) a surfactant.

The present invention relates to an improved method for producing chemiluminescence which comprises reacting a peroxide compound and a peroxidase enzyme with an acridan of the formula:

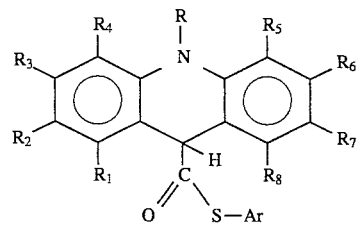

wherein R is selected from alkyl, heteroalkyl and aralkyl groups, wherein $R_1$ through $R_8$ are independently selection from hydrogen and groups which allow the production of light and wherein Ar is selected from substituted and unsubstituted aryl (particularly phenyl, naphthyl and biphenyl), and heteroaryl (particularly pyridyl, quinolyl and xanthenyl) groups which allow the production of light from the acridan by reaction with a peroxide and a peroxidase.

The present invention also relates to an improved method for detecting a peroxidase enzyme or an analyte linked to or capable of being linked to a peroxidase enzyme in an assay procedure by a chemiluminescent reaction, the improvement which comprises reacting an acridan with a peroxide and a peroxidase enzyme to produce light for detecting the analyte wherein the acridan is of the following formula:

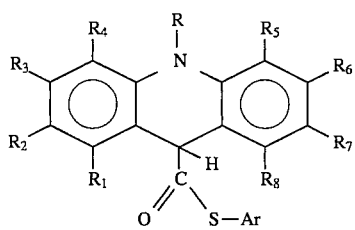

wherein R is selected from alkyl, heteroalkyl and aralkyl groups, wherein $R_1$ through $R_8$ are independently selected from hydrogen and groups which allow the production of light and wherein Ar is selected from substituted and unsubstituted aryl (particularly phenyl, naphthyl and biphenyl), and heteroaryl (particularly pyridyl, quinolyl and xanthenyl) groups which allow the production of light from the acridan by reaction with a peroxide and a peroxidase.

The present invention also relates to an improved method for detecting a peroxidase enzyme or an analyte linked to or capable of being linked to a peroxidase enzyme in an assay procedure by a chemiluminescent reaction, the improvement which comprises a) providing a reagent composition which generates light in the presence of a peroxidase which comprises: an acridan of the formula:

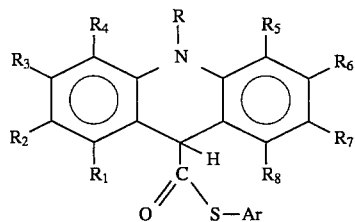

wherein R is selected from alkyl, heteroalkyl and aralkyl groups, wherein $R_1$ through $R_8$ are independently selected from hydrogen and groups which allow the production of light and wherein Ar is selected from substituted and unsubstituted aryl (particularly phenyl, naphthyl and biphenyl), and heteroaryl (particularly pyridyl, quinolyl and xanthenyl) groups which allow the production of light from the acridan by reaction with a peroxide and a peroxidase; a peroxide compound which participates in the reaction of the acridan with the peroxidase; an enhancer substance which may be a phenolic compound which enhances the light production from the acridan; a chelating agent which prevents the peroxide compound from reacting prior to addition of the peroxidase to the composition; and a surfactant; and b) adding a peroxidase to the reagent composition so that light is produced for detecting the analyte.

The present invention also relates to a kit for detecting an analyte in an assay procedure by a chemiluminescent reaction to produce light which comprises in separate containers:

a) an acridan of the formula:

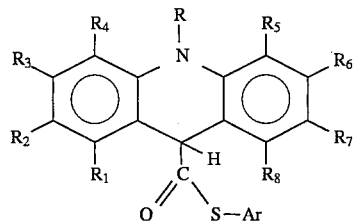

wherein R is selected from alkyl, heteroalkyl and aralkyl groups, wherein $R_1$ through $R_8$ are independently selected from hydrogen and groups which allow the production of light and wherein Ar is selected from substituted and unsubstituted aryl (particularly phenyl, naphthyl and biphenyl) and heteroaryl (particularly pyridyl, quinolyl and xanthenyl) groups which allow the production of light from the acridan by reaction with a peroxide and a peroxidase; a peroxide; optionally an enhancer substance which may be a phenolic compound which enhances the light production from the acridan; a chelating agent which prevents the peroxide compound from reacting prior to addition of the peroxidase to the composition; and a surfactant; and b) a peroxidase enzyme, wherein the light is detected in the assay procedure by reacting the reagent composition with the peroxidase.

The present invention also relates to an improved method for detecting hydrogen peroxide in an assay procedure by a chemiluminescent reaction, the improvement which comprises reacting hydrogen peroxide and a peroxidase enzyme with an acridan of the formula:

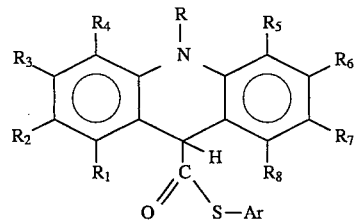

wherein R is selected from alkyl, heteroalkyl and aralkyl groups, wherein $R_1$ through $R_8$ are independently selected from hydrogen and groups which allow the production of light and wherein Ar is selected from substituted and unsubstituted aryl (particularly phenyl, naphthyl, biphenyl) and heteroaryl (particularly pyridyl, quinolyl and xanthenyl) groups which allow the production of light from the acridan by reaction with a peroxide and a peroxidase.

The invention involves improved aryl N-alkylacridanthiocarboxYlate derivatives with superior properties in one or more of the following characteristics: longer duration of light emission, higher intensity of light emission, faster rate of rise of light emission to the maximum value, lowered background chemiluminescence, improved signal/background ratio, extended storage stability of a chemiluminescent detection reagent composition, enhanced light emission on a membrane or other properties. The particular combinations of the groups R, $R_1$ through $R_8$ and Ar can be chosen so as to provide a compound with one or more properties which are optimal for particular applications.

Acridan compounds with Ar groups consisting of phenyl substituted in the para position with a fluoro, trifluoromethyl, hydroxy or methoxy group, for example, achieve a rapid build-up of light intensity and high peak light intensity.

Groups which are contemplated as substituents also include alkyl, alkenyl, alkynyl, aralkyl, aryl, alkoxyl, alkoxyalkyl, halogen, carbonyl, carboxyl, carboxamide, cyano, trifluoromethyl, trialkylammonium and nitro groups. When extended storage stability of a chemiluminescent reagent composition containing an aryl N-alkylacridanthiocarboxylate derivative is desired, one or more of the $R_1$ through $R_8$ groups may be a group such as an alkyl, alkoxy or aryloxy group.

Examples of some preferred compounds are:

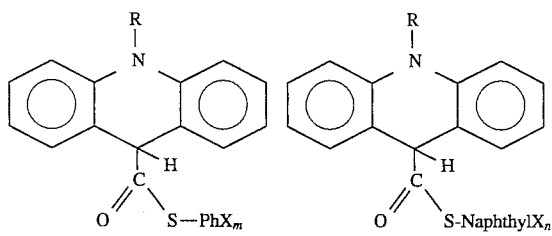

wherein R is an alkyl, aralkyl or heteroalkyl group, wherein X is a group selected from halogen, trihalomethyl, nitro, cyano, ammonium, carboxyl, carboxamide, amino, substituted amino, aryl, alkyl, alkenyl, alkynyl, alkoxy, and hydroxy and wherein m is 0 to 5 and n is 0 to 7.

Another class of preferred compounds is:

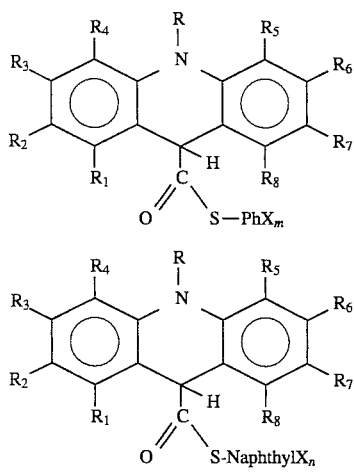

wherein R, X, m and n are as defined above and $R_1$ through $R_8$ are independently selected from hydrogen and groups which allow light to be produced and wherein at least one of $R_1$ through $R_8$ is not hydrogen. More preferred are compounds wherein at least one of $R_1$ through $R_8$ is an alkoxy group.

Reaction of certain aryl N-alkylacridanthiocarboxylate derivatives of the present invention with a peroxide and a peroxidase enzyme produces chemiluminescence with superior properties for assay applications. The chemiluminescence is believed to arise from the excited state of N-alkylacridone or the substituted N-alklyacridone product as shown in the generalized reaction below. Derivatives of aryl N-alkylacridanthiocarboxylate found to undergo the reaction include substituted and unsubstituted aryl thioesters, especially phenyl and naphthyl thioesters.

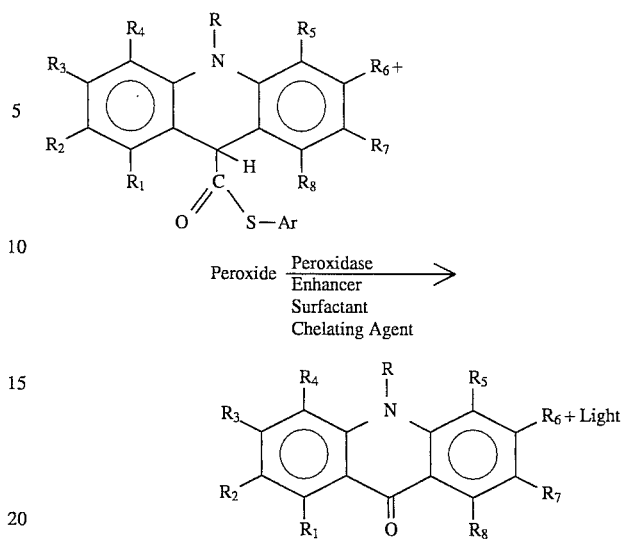

The present invention involves a method of generating chemiluminescence from the oxidation of aryl N-alkylacridanthiocarboxylate derivatives by the action of a peroxidase enzyme, a peroxide compound and enhancers. The invention also relates to the use of this method to detect the peroxidase enzyme with high sensitivity. Further, the invention relates to the use of the method to detect and quantitate various biological molecules which are bound to this enzyme by chemical bonds or through physical interactions. Further, the invention relates to the use of the method to detect and quantitate various biological molecules which are capable of being bound to this enzyme, for example, by using a biotin-labeled analyte and streptavidin-peroxidase conjugate. Other high affinity binding pairs well known in the art such as fluorescein and anti-fluorescein, digoxigenin and anti-digoxigenin or complementary nucleic acid sequences may also be readily employed as a means of linking a peroxidase enzyme to an analyte for the purpose of practicing this invention. The intensity of the resulting chemiluminescence provides a direct measure of the quantity of labeled organic or biological molecule. For example, the method may be used to detect haptens, antigens and antibodies by the technique of immunoassay, proteins by Western blotting, DNA and RNA by Southern and Northern blotting, respectively. The method may also be used to detect DNA in DNA sequencing applications. The method may additionally be used to detect hydrogen peroxide generated by enzymes such as cholesterol oxidase, glucose oxidase, glucose-6-phosphate dehydrogenase, galactose oxidase, galactose-6-phosphate dehydrogenase, and amino acid oxidase. The method may also therefore be used as a means to detect the enzymes mentioned above which generate hydrogen peroxide.

The reaction of the present invention may advantageously be carried out in solution such as an aqueous buffer or on the surface of a solid support such as a bead, tube, microwell plate or a membrane. Suitable buffers include any of the commonly used buffers capable of maintaining a pH in the range of about 6 to about 10 for example, phosphate, borate, carbonate, tris(hydroxymethylamino)methane, glycine, tricine, 2-amino-2-methyl-1-propanol, diethanolamine and the like. The preferred method of practicing the invention in this regard is determined by the requirements of the particular intended use as in for example, immunoassays, Western blotting, Southern blotting etc. When the detection is to be performed on a membrane, said membrane may optionally be provided in a kit.

The detection of chemiluminescence from the oxidation of an aryl N-alkylacridanthiocarboxylate derivative by a peroxide and a peroxidase enzyme can be accomplished with good sensitivity. Enhancement of this reaction by incorporation of chemiluminescence-enhancing substances permits the measurement of chemiluminescence using still lower levels of the peroxidase enzyme. Coupling this enzyme to a biological molecule of interest then permits the detection of this biological molecule with great sensitivity.

Incorporation of certain substituted phenolic compounds either alone or in combination with surfactants into the reaction mixture enhances the chemiluminescence produced in the presence of added peroxidase and peroxide. Enhancement may take the form of either a higher light intensity, or light emission of longer duration or both. Phenolic compounds which are known to enhance other peroxidase reactions and which are found to enhance the amount of chemiluminescence in the present invention include but are not limited to: p-phenylphenol, p-iodophenol, p-bromophenol, p-hydroxycinnamic acid, 2-naphthol and 6-bromo-2-naphthol. It will be obvious to one knowledgeable in the art that other phenolic and aromatic amine compounds fall within the scope of this invention. Such compounds include firefly luciferin, 6-hydroxybenzothiazole, 2-cyano-6-hydroxy-benzothiazole, 4-(4-hydroxyphenyl)thiazole, p-chlorophenol, 2,4-dichlorophenol, 2-chloro-4-phenylphenol, 1-bromo-2-naphthol 1,6-dibromo-2-naphthol, 2-hydroxy-9-fluorenone, 6-hydroxybenzoxazole derivatives, and 4-hydroxy-3-[3-(4-hydroxyphenyl)-1-oxo-2-propenyl]-2H-1-benzopyran-2-one as are described in, for example, G. Thorpe, L. Kricka, in Bioluminescence and Chemiluminescence, New Perspectives, J. Scholmerich, et al, Eds., pp. 199–208 (1987), M. Ii, H. Yoshida, Y. Aramaki, H. Masuya, T. Hada, M. Terada, M. Hatanaka, Y. Ichimori, Biochem. Biophys. Res. Comm., 193(2), 540–5 (1993), and in U.S. Pat. Nos. 5,171,668 and 5,206,149 which are incorporated herein by reference. It will also be obvious to one knowledgeable in the art that certain organoboron compounds such as those described in PCT/GB93/00271 may be enhancers and are included in the scope of the present invention by reference.

Additives which suppress the generation of background chemiluminescence from the reaction of hydrogen peroxide and aryl N-alkylacridanthiocarboxylate derivatives in the absence of peroxidase enzymes are employed to further improve the utility of the invention. It has also been found that certain surfactants such as anionic, cationic and nonionic surfactants improve the sensitivity of detection of the peroxidase enzyme in assays of the present invention by providing a larger chemiluminescence signal and a better signal to background ratio. The improvement also occurs through minimizing the background chemiluminescence in the absence of added peroxidase, possibly due to a slowing of the autoxidative decomposition of the acridan derivative.

The preferred amounts of the various components of a composition of the present invention are set forth in Table I.

TABLE I

| Acridan | 0.01–10 mM |
| Phenol enhancer | 0.001–10 mM |
| Surfactant | 0.005–5% |
| Peroxide | 0.01–10 mM |
| Chelating agent | 0.01–5 mM |

The present invention involves a solution in an aqueous buffer containing 1) a phenol enhancer or a salt of a phenol enhancer, 2) a peroxide compound wherein the peroxide compound may be, for example, hydrogen peroxide, urea peroxide, or a perborate salt, 3) an acridan compound of the invention, 4) a cation complexing agent wherein the agent may be selected from the group consisting of chelating agents such as ethylenediaminetetraacetic acid (EDTA), diethylenetriaminepentaacetic acid (DTPA), or ethylenebis(oxyethylenenitrilo)-tetraacetic acid (EGTA) and their salts, and 5) a surfactant such as the anionic surfactant sodium dodecyl sulfate (SDS), or preferably a nonionic surfactant such as polyoxyethylenated alkylphenols, polyoxyethylenated alcohols, polyoxyethylenated ethers, polyoxyethylenated sorbitol esters and the like.

In a preferred method of practicing the present invention, an aqueous buffer solution with a pH in the range of 6–8.5 containing a phenol compound such as p-phenylphenol at a final concentration from about 0.01M to $1\times10^{-6}$M, a nonionic surfactant at a final concentration from about 5% to 0.005% (v/v), a peroxide source such as hydrogen peroxide or, preferably, a perborate salt or urea peroxide and a cation complexing agent such as EDTA at a final concentration from about $1\times10^{-3}$M to $1\times10^{-5}$M is mixed with a second solution containing an acridan compound of the invention to achieve a final concentration from about 0.001M to $1\times10^{-5}$M to form the detection reagent solution. This solution is contacted with the peroxidase enzyme which may either be in solution or adhered to a solid support. Optimum concentrations of reagents must be determined individually for each composition. The concentration of acridan compound and enhancer in particular should be optimized with care for each case in order to produce the maximum enhancement of light emission. The detection reaction may be performed over a range of temperatures including at least the range 20°–40° C. Detection may be conveniently and advantageously carried out at ambient temperature.

It has further been discovered that the storage stability of detection reagent compositions with certain of the acridans of the present invention is unexpectedly greater than acridan compounds previously disclosed in applicant's copending applications 08/061,810 filed on May 17, 1993 and 08/205,093, filed Mar. 2, 1994. Extended storage stability can result in savings in reagents and cost. Detection reagents of the present invention stored in this manner retain the ability to generate the same quantity of chemiluminescence by the action of a peroxidase enzyme for longer periods of time. Contrary to expectation, some of the reagents of the present invention bearing a thioester leaving group demonstrate greater stability than similar acridans bearing an aryl ester leaving group. Further, storage stability of aqueous solutions of acridans of the present invention differ substantially from the behavior of acridan and acridinium aryl esters described in the aforementioned U.S. Pat. Nos. 5,284,951 and 5,284,952. Acridans disclosed in these two patents require three substituents in the aryl ester moiety, two ortho electron-donating substituents and a meta or para electron-withdrawing substituent in order to achieve useful storage stability. Acridans of the present invention do not require any ortho electron-donating substituents for stabilization. Moreover the stability of aqueous solutions of acridans of the present invention can be extended still further by exclusion of oxygen from the solution and by storing at a temperature below about 10° C.

Significant advantages of aryl N-alkylacridanthiocarboxylate derivatives and compositions of the present invention containing them include improved light generation and hence increased sensitivity of detection of the peroxidase enzyme and increased stability of the aryl N-alkylacridanthiocarboxylate derivative to hydrolytic decomposition. Comparative experiments show a 100-fold lowering of the detection limit of HRP using a reagent composition of this invention compared to a detection reagent containing luminol and an enhancer. Aryl N-alkylacridanthiocarboxylate derivatives (-SAr) are also unexpectedly superior to alkyl N-alkylacridanthiocarboxylate derivatives (-SR) in light generating ability. An additional advantage is the wider dynamic range of measurement of peroxidase concentration. Still another advantage of the use of certain aryl N-alkylacridanthiocarboxylate derivatives compared to prior compounds is the extended duration of chemiluminescence. Extending the duration simplifies the measurement by obviating the need for precise reaction timing and increases the sensitivity of detection when using film-based detection methods.

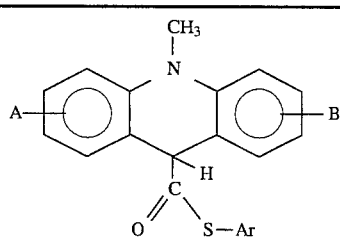

| Compound | A | B | Ar |
|---|---|---|---|
| 5a | H | H | Phenyl |
| 5b | H | H | 4'-Hydroxyphenyl |
| 5c | H | H | 2',6'-Dimethylphenyl |
| 5d | H | H | 4'-Fluorophenyl |
| 5e | H | H | 4'-Trifluoromethylphenyl |
| 5f | H | H | 4'-Methoxyphenyl |
| 5g | H | H | 2',6'-Dichlorophenyl |
| 5h | H | H | 2-Naphthyl |
| 5i | 2-OCH$_3$ | 7-OCH$_3$ | 2-Naphthyl |
| 5j | 3-OCH$_3$ | H | 4'-Fluorophenyl |

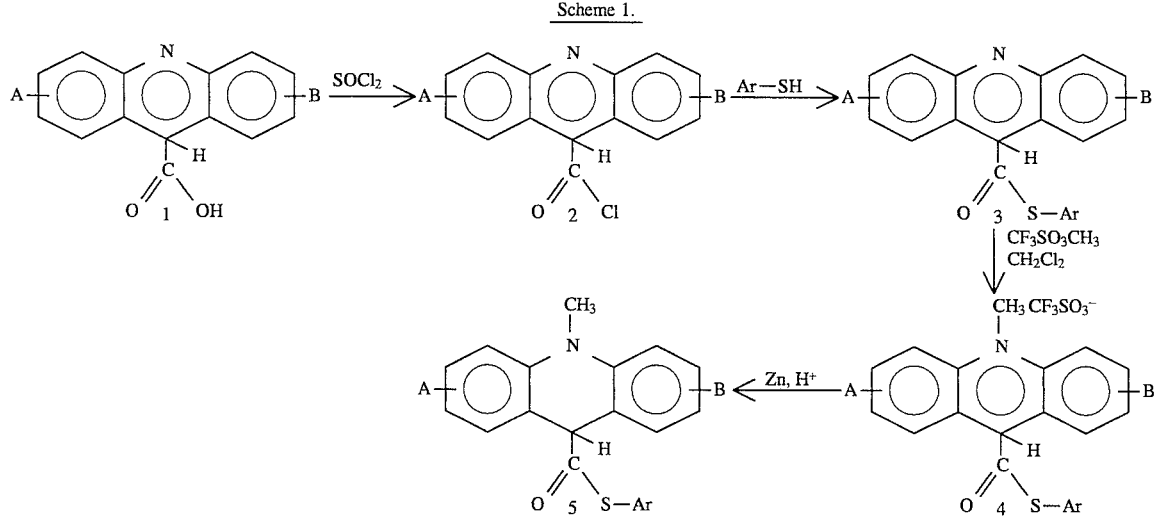

Scheme 1.

EXAMPLES

Example 1

Synthesis of Acridan Derivatives.

Acridancarboxylic acid derivatives 5a-j were synthesized according to the method shown in Scheme 1 from the corresponding acridine-9-carboxylic acid with the exception of compound 5b whose synthesis is described in detail in example 3. In the structure shown below, the substituents A and B correspond to the groups $R_1$ through $R_8$ in formula (II). All other ring substituents are hydrogen.

The corresponding acridine-9-carboxylic acid compounds were prepared by the reaction sequence depicted in Scheme 2. (G. Zomer, J. Stavenuiter, R. Van Den Berg, E. Jansen, In *Luminescence Techniques in Chemical and Biochemical Analysis*, W. Baeyens, D. De Keukeleire, K. Korkidis, eds., Dekker, New York, 505–521, (1991); R. Stollé, J. Prakt. Chem., 105, 137, (1922)).

| Compound | A | B |
|---|---|---|
| 1a | H | H |
| 1i | 2-OCH$_3$ | 7-OCH$_3$ |

| Compound | A | B |
|---|---|---|
| 1j | 3-OCH$_3$ | H | pressure to obtain 2a, 2i or 2j as a yellow solid which was used directly for formation of compound 3a, 3c–j.

General Procedure for Synthesis of Compounds 3a, 3c–j.

Compound 2 derived from the corresponding compound 1 shown in the table was dissolved in methylene chloride and pyridine (2–3 eq.) under argon. A solution of the phenol (1–1.5 eq.) in methylene chloride was added dropwise. The solution was stirred overnight at room temperature then diluted with more methylene chloride (100 mL) and washed with water (3×50 mL). The organic layer was dried over Na$_2$SO$_4$ and concentrated to obtain the product.

Scheme 2.

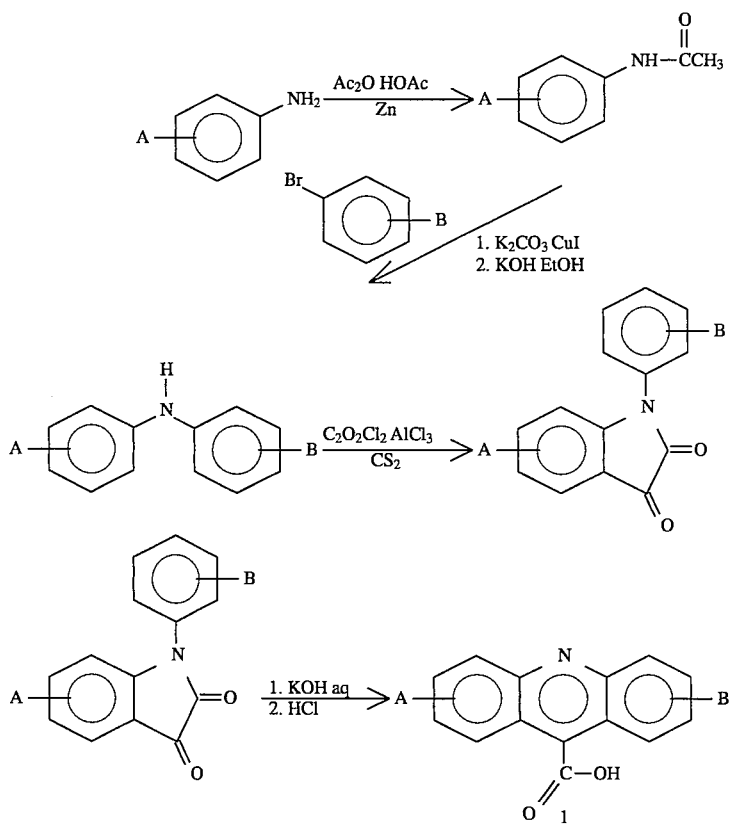

General Procedure for Synthesis of Compounds 2a, 2i and 2j. Compound 1a, 1i or 1j (0.2–0.5 g) was suspended in excess thionyl chloride (3–10 mL) and reaction mixture was refluxed for 3h. The solvent was removed under reduced

| Compound 3 | Compound 1 | SOCl$_2$ | Thiophenol | | Pyridine |
|---|---|---|---|---|---|
| a | a | 0.20 g | 7 mL | Thiophenol | 0.15 g | 0.14 mL |
| c | a | 0.50 g | 10 mL | 2,6-Dimethyl- | 0.34 g | 0.44 g |
| d | a | 0.50 g | 7 mL | 4-Fluoro- | 0.31 g | 0.44 g |
| e | a | 0.50 g | 10 mL | 4-Trifluoromethyl- | 0.427 g | 0.44 g |
| f | a | 0.50 g | 10 mL | 4-Methoxy | 0.336 g | 0.44 g |
| g | a | 0.50 g | 7 mL | 2,6-Dichloro- | 0.44 g | 0.44 g |
| h | a | 0.50 g | 10 mL | 2-Naphthol | 0.395 g | 0.44 g |
| i | i | 0.90 g | 5 mL | 2-Naphthol | 0.51 g | 2.0 mL* |
| j | j† | 2.50 g | 30 mL | 4-Fluoro- | 1.90 g | 1.17 g |

| Compound 3 | Compound 1 | SOCl$_2$ | Thiophenol | Pyridine |
| --- | --- | --- | --- | --- |

*Triethylamine used in place of pyridine.
†Mixture of 1-methoxy- and 3-methoxyacridine carboxylic acid isomers was used. The desired compound was separated by chromatography.

General Procedure for Synthesis of Compounds 4a, 4c–j. Compound 3 (1–2 mmol) was dissolved in methylene chloride (5–10 ml) under argon and methyl trifluoromethanesulfonate (5–10 eq.) was added. The solution was stirred overnight at room temperature to yield a thick yellow precipitate. This precipitate was filtered, washed with ether and dried to obtain the product as yellow crystals.

| Compound 4 | Compound 3 | CH$_2$Cl$_2$ | CH$_3$OSO$_2$CF$_3$ | |
| --- | --- | --- | --- | --- |
| a | a | 0.28 g | 10 mL | 1.00 mL | 10 eq. |
| c | c | 0.30 g | 10 mL | 0.692 mL | 7 eq. |
| d | d | 0.30 g | 10 mL | 0.713 mL | 7 eq. |
| e | e | 0.40 g | 7 mL | 0.826 mL | 7 eq. |
| f | f | 0.35 g | 10 mL | 0.803 mL | 7 eq. |
| g | g | 0.30 g | 7 mL | 0.883 mL | 10 eq. |
| h | h | 0.30 g | 10 mL | 0.633 mL | 7 eq. |
| i | i | 0.20 g | 10 mL | 1.0 mL | 17 eq. |
| j | j | 0.50 g | 10 mL | 1.0 mL | 6.5 eq. |

General Procedure for Synthesis of Compounds 5a, 5c, 5h and 5j (Method A). Compound 4 (0.2–0.3 mmol) was suspended in absolute ethanol (15–30 mL) and solution was refluxed for 10 min to obtain a clear solution. Excess ammonium chloride (10–50 eq.) was added by portions to the solution followed by zinc (equimolar ratio to the amount of NH$_4$Cl) causing immediate decolorization of the solution. The colorless solution was refluxed for 30 min. The cooled solution was filtered and the precipitate washed with ethanol (3×20 mL). The solution was concentrated to obtain a creamy solid which was redissolved in methylene chloride and washed with water (3×50 mL). Crude material obtained after evaporation of methylene chloride was chromatographed on silica gel (ethyl acetate/hexane) to yield the pure product as a white solid.

General Procedure for Synthesis of Compounds 5d, 5e, 5.f, 5g and 5i (Method B). Compound 4 (0.3–0.6 mmol) was dissolved in 10 mL of glacial acetic acid to obtain a yellow solution and zinc was added (100 eq.) causing immediate decolorization of the solution. After 5 min stirring at room temperature, TLC of the reaction mixture showed a nonpolar material. The acetic acid was decanted and the solid washed with methylene chloride. The combined organic solutions were evaporated to obtain a crude solid which was redissolved in methylene chloride and washed with 2 or 3–50 mL portions of water. The crude material obtained after evaporation of methylene chloride was chromatographed on silica gel (20–30% ethyl acetate/hexane) to yield the pure product as a white solid.

| Method | Compound 5 | Compound 4 | Zinc | Ethanol | NH$_4$Cl | Acetic Acid |
| --- | --- | --- | --- | --- | --- | --- |
| A | a | a | 0.15 g | 2.00 g | 30 mL | 1.6 g | — |
| A | c | c | 0.20 g | 1.28 g | 20 mL | 1.28 g | — |
| B | d | d | 0.20 g | 1.3 g | — | — | 10 mL |
| B | e | e | 0.30 g | 1.78 g | — | — | 10 mL |
| B | f | f | 0.23 g | 1.47 g | — | — | 10 mL |
| B | g | g | 0.19 g | 2.2 g | — | — | 10 mL |
| A | h | h | 0.25 g | 1.5 g | 25 mL | 1.24 g | — |
| B | i | i | 0.05 g | 1.0 g | 10 mL | 1.0 g | — |
| A | j | j | 0.20 f | 1.0 g | 30 mL | 1.0 g | — |

Example 2

Synthesis of Compound 5a.

Phenyl acridine-9-thiocarboxylate (3a). The substantially pure product was further dried in vacuum. $^1$H NMR (CDCl$_3$) δ7.48–8.32 (m, 13H); $^{13}$C NMR (CDCl$_3$) δ121.40, 124.76, 126.79, 127.32, 129.59, 129.93, 130.24, 130.57, 134.61, 142.18, 148.54, 193.91.

Phenyl 10-methylacridinium-9-thiocarboxylate trifluoromethanesulfonate (4a). $^1$H NMR (acetone-d$_6$) δ5.20 (s, 3H), 7.61–7.86 (m, 5H), 8.20–9.03 (m, 8H).

Phenyl 10-methylacridan-9-thiocarboxylate (5a). Method A. $^1$H NMR (CDCl$_3$) δ3.45 (s, 3H), 5.08 (s, 1H), 6.98–7.36 (m, 13H). $^{13}$C NMR (CDCl$_3$) δ33.52, 58.28, 113.79, 121.29, 121.41, 129.61, 129.81, 130.58, 135.13, 143.49, 150.37, 197.17.

Example 3.

Synthesis of Compound 5b. 4'-(tert-Butyldimethylsilyloxy)thiophenol. To a solution of 4-hydroxythiophenol (1.0 g, 7.9 mmol) and tert-butyldimethylsilyl chloride (1.2 g, 7.9 mmol) in 5 mL of dry DMF was gradually added imidazole (1.07 g, 0.015 mol) and the solution was stirred for 1 h. TLC analysis (silica gel, 30% ethyl acetate/hexane) showed completion of reaction. The solution was poured into 25 mL of water and extracted with 3×25 mL of hexane. The combined hexane solutions were washed with 2×50 mL of water and dried over anhydrous Na$_2$SO$_4$. Evaporation of solvent gave an oil (1.8 g) as the product. $^1$H NMR (CDCl$_3$) δ0.162 (s, 6H), 0.954 (s, 9H), 3.35 (s, 1H), 6.69–6.73 (d, 2H), 7.16–7.19 (d, 2H).

4'-tert-Butyldimethylsilyloxyphenyl acridine-9-thiocarboxylate. Acridine-9-carboxylic acid (1a) (1.45 g, 6.5 mmol) was suspended in thionyl chloride (10 ml) and the reaction mixture was refluxed for 3 h. The solvent was removed under reduced pressure to obtain a yellow solid which was dissolved in methylene chloride and pyridine (4 mL) under argon. 4-(tert-Butyldimethylsilyloxy) thiophenol (1.85 g, 7.6 mmol) was added and the solution stirred overnight at room temperature. The reaction mixture was diluted with more methylene chloride (200 mL) and washed with water (3×50 mL). The organic layer was dried over Na$_2$SO$_4$ and concentrated to obtain the crude product which was further purified by column chromatography on silica gel using 20% ethyl acetate/hexane. $^1$H NMR (CDCl$_3$) δ0.216 (s, 6H), 0.987 (s, 9H), 6.85–8.26 (m, 12H); $^{13}$C NMR (CDCl$_3$) δ–4.37, 18.21, 25.66, 118.17, 121.22, 121.37, 124.80, 127.11, 129.96, 130.35, 136.15, 142.22, 148.52, 157.59, 195.08.

4'-tert-Butyldimethylsilyloxyphenyl 10-methylacridinium-9-thiocarboxylate trifluoromethanesulfonate and 4'-hydroxyphenyl 10-methylacridinium-9-thiocarboxylate trifluoromethanesulfonate. To a solution of 4-tert-butyldimethylsilyloxyphenyl acridine-9-thiocarboxylate (1 g, 2.2 mmol) in methylene chloride (15 ml) was added methyl trifluoromethanesulfonate (7.2 g, 0.04 mol) under argon. The reaction mixture was stirred at room temperature for 2 days to yield a yellow precipitate. This precipitate was filtered and dried to obtain yellow crystals which consisted of a mixture (45:55) of silylated and desilylated salt forms: 4'-tert-butyldimethylsilyloxyphenyl 10-methylacridinium-9-thiocarboxylate trifluoromethanesulfonate; $^1$H NMR (acetone-d$_6$) δ0.261 (s, 6H), 1.003 (s, 9H), 5.17 (s, 3H), 7.04–7.07 (d, 2H), 7.67–7.70 (d, 2H), 8.18 –9.02 (m, 8H); 4'-hydroxyphenyl 10-methylacridinium-9-thiocarboxylate trifluoromethanesulfonate; $^1$H NMR (acetone-d$_6$) δ5.16 (s, 3H), 6.95–6.99 (d, 2H ), 7.56–7.59 ( d, 2H), 8.18–9.00 (m, 8H), 9.12 (s, 1H).

4'-Hydroxyphenyl 10-methylacridan-9-thiocarboxylate (5b). Method A. A mixture of 4'-tert-butyldimethylsilyloxyphenyl 10-methylacridinium-9-thiocarboxylate trifluoromethanesulfonate and 4'-hydroxyphenyl 10-methyacridinium-9-thiocarboxylate trifluoromethanesulfonate (1 g) was suspended in absolute ethanol (75 ml) and the mixture was refluxed for 10 min to effect solution. Ammonium chloride (8.0 g, 0.149 mol) was added by portions to the solution followed by zinc (9.5 g, 0.146 mol). The yellow color of solution disappeared immediately after the addition of zinc. The colorless solution was refluxed for 3 h. TLC of the reaction mixture showed complete conversion to two nonpolar materials. The solution was filtered and the inorganic solids were washed with ethanol (3×20 ml). The combined organic solutions were concentrated to obtain a solid which was redissolved in methylene chloride. The methylene chloride was washed with water (3×50 mL), dried over anhydrous Na$_2$SO$_4$ and concentrated to yield a mixture of silylated and desilylated products. This mixture was separated and purified by chromatography on silica gel using 30% ethyl acetate/hexane to yield the product as a white solid. $^1$H NMR (acetone-d$_6$) δ3.39 (s, 3H), 5.17 (s, 1H), 6.82–7.37 (m, 12 H), 8.73 (bs, 1H); $^{13}$C NMR (acetone-d$_6$) δ33.01, 57.57, 113.23, 116.45, 117.91, 120.86, 129.03, 130.02, 136.40, 142.88, 149.80, 158.79, 197.64.

Example 4.

Synthesis of Compound 5c.

2',6'-Dimethylphenyl acridine-9-thiocarboxylate (3c). $^1$H NMR (CDCl$_3$) δ2.68 (s, 6H), 7.32–7.38 (m, 3H), 7.67–8.47 (m, 8H).

2',6'-Dimethylphenyl 10-methylacridinium-9-thiocarboxylate trifluoromethanesulfonate (4c). $^1$H NMR (acetone-d$_6$) 2.68 (s, 6H), 5.23 (s, 3H), 7.40–7.47 (m, 3H), 8.26–9.07 (m, 8H).

2',6'-Dimethylphenyl 10-methylacridan-9-thiocarboxylate (5c). Method A. $^1$H NMR (CDCl$_3$) δ2.09 (s, 6H), 3.46 (s, 3H), 5.08 (s, 1H), 6.97–7.36 (m, 11H).

Example 5.

Synthesis of Compound 5d.

4'-Fluorophenyl acridine-9-thiocarboxylate (3d). $^1$H NMR (CDCl$_3$) δ7.17–7.47 (m, 4H), 7.67–8.29 (m, 12H).

4'-Fluorophenyl 10-methylacridinium-9-thiocarboxylate trifluoromethanesulfonate (4d). $^1$H NMR (acetone-d$_6$) δ5.19 (s, 3H), 7.38–9.04 (m, 12H).

4'-Fluorophenyl 10-methylacridan-9-thiocarboxylate (5d). Method A. $^1$H NMR (CDCl$_3$) δ3.46 (s, 3H), 5.08 (s, 1H), 6.96–7.38 (m, 12H).

Example 6

Synthesis of Compound 5e. 4'-Trifluoromethylphenyl acridine-9-thiocarboxylate (3e). $^1$H NMR (CDCl$_3$) δ7.64–8.31 (m, 12H).

4'-Trifluoromethylphenyl 10-methylacridinium-9-thiocarboxylate trifluoromethanesulfonate (4e). $^1$H NMR (acetone-d$_6$) δ5.23 (s, 3H), 8.01–9.07 (m, 12H).

4'-Trifluoromethylphenyl 10-methylacridan-thiocarboxylate (5e ). Method A. $^1$H NMR (CDCl$_3$) δ3.46 (s, 3H), 5.10 (s, 1H), 7.00–7.55 (m, 12H).

Example 7

Synthesis of Compound 5f. 4'-Methoxyphenyl acridine-9-thiocarboxylate (3f). $^1$H NMR (CDCl$_3$) δ3.86 (s,3H), 6.99–7.02 (d, 2H), 7.54–7.57 (d, 2H), 7.61–8.28 (m, 8H).

4'-Methoxyphenyl 10-methylacridinium-9-thiocarboxylate trifluoromethanesulfonate (4f). $^1$H NMR (acetone-d$_6$) δ3.90 (s, 3H), 5.19 (s, 3H), 7.12–7.15 (d, 2H), 7.73–7.76 (d, 2H), 8.20–9.04 (m, 8H).

4'-Methoxyphenyl 10-methylacridan-9-thiocarboxylate (5f). Method A. $^1$H NMR (CDCl$_3$) δ3.45 (s, 3H), 3.76 (s, 3H), 5.07 (s, 1H), 6.81–7.35 (m, 12H).

Example 8

Synthesis of Compound 5g. 2',6'-Dichlorophenyl acridine-9-thiocarboxylate (3 g). $^1$H NMR (CDCl$_3$) δ7.44–7.62 (m, 3H), 7.66–8.36 (m, 8H).

2',6'-Dichlorophenyl 10-methylacridinium-9-thiocarboxylate trifluoromethanesulfonate (4 g). $^1$H NMR (acetone-d$_6$) δ5.19 (s, 3H), 7.38–9.04 (m, 11H).

2',6'-Dichlorophenyl 10-methylacridan-9-thiocarboxylate (5 g). Method A. $^1$H NMR (CDCl$_3$) δ3.47 (s, 3H), 5.08 (s, 1H), 6.99–7.38 (m, 11H).

Example 9

Synthesis of Compound 5h. 2'-Naphthyl acridine-9-thiocarboxylate (3h). $^1$H NMR (CDCl$_3$) δ7.57–8.29 (m, 15H).

2'-Naphthyl 10-methylacridinium-9-thiocarboxylate trifluoromethanesulfonate (4h). $^1$H NMR (acetone-d$_6$) 5.19 (s, 3H), 7.67–9.03 (m, 15H).

2'-Naphthyl 10-methylacridan-9-thiocarboxylate (5h). Method A. $^1$H NMR (CDCl$_3$) δ3.47 (s, 3H), 5.13 (s, 1H), 7.01–7.79 (m, 15H).

Example 10

Synthesis of Compound 5i. 2'-Naphthyl 2,7-dimethoxyacridine-9-thiocarboxylate (3i). $^1$H NMR (CDCl$_3$) δ4.024 (s, 6H), 7.265–7.281 (t, 2H), 7.425–7.466 (dd, 2H), 7.564–7.669 (m, 3H), 7.86–7.97 (m, 3H), 8.095–8.125 (d, 3H).

2'-Naphthyl 2,7-dimethoxy-10-methylacridinium-9-thiocarboxylate trifluoromethanesulfonate (4i). $^1$H NMR (DMSO-d$_6$) δ4.146 (s, 6H), 4.876 (s, 3H), 7.472–7.480 (d, 2) 7.669–7.708 (m, 2H), 7.844–7.878 (dd, 1H), 8.049–8.155 (m, 5H), 8.481 (s, 1H), 8.800–8.835 (d, 2H).

2'Naphthy 2,7-dimethoxy-10-methylacridan-9-thiocarboxylate (5i). Method A. $^1$H NMR (CDCl$_3$) δ3.401 (s, 3H), 3.813 (s, 6H), 5.042 (s, 1H), 6.902–6.926 (m, 6H), 7.265–7.300 (dd, 1H), 7.428–7.468 (m, 2H), 7.708–7.790 (m, 4H).

Example 11

Synthesis of Compound 5j.

4'-Fluorophenyl 3-methoxyacridine-9-thiocarboxylate (3j). The product was further purified by column chromatography on silica gel using 15% ethyl acetate/hexane to yield the product. $^1$H NMR (CDCl$_3$) δ4.034 (s, 3H), 7.171–7.230 (t, 2H), 7.307–7.346 (dd, 1H), 7.486–7.494 (d, 1H), 7.561–7.651 (m, 3H), 7.787–7.84 (m, 1H), 7.989–8.021 (d, 1H), 8.068–8.094 (d, 1H), 8.174–8.202 (d, 1H).

4'-Fluorophenyl 3-methoxy-10-methylacridinium-9-thiocarboxylate trifluoromethane-sulfonate (4j). $^1$H NMR (DMSO-d$_6$) δ4.259 (s, 3H), 4.769 (s, 3H), 7.476–7.535 (t, 2H), 7.707–7.746 (dd, 1H), 7.863–7.869 (d, 1H), 7.937–8.054 (m, 3H), 8.398–8.452 (t, 1H), 8.475–8.507 (d, 2H), 8.766–8.797 (d, 1H).

4'-Fluorophenyl 3-methoxy-10-methylacridan-9-thiocarboxylate (5j). Method A. $^1$H NMR (CDCl$_3$) δ3.434 (s, 3H), 3.857 (s, 3H), 5.025 (s, 1H), 6.540–6.601 (m, 2H), 6.963–7.037 (m, 4H), 7.193–7.370 (m, 5H).

Chemiluminescence Measurements

The experiments in the following examples were performed using either a Turner Designs TD-20e (Sunnyvale, Calif.) luminometer fitted with neutral density filter for light attenuation or a Labsystems Luminoskan (Helsinki, Finland) luminometer. Data collection, analysis and display were software controlled.

Example 12

Comparison of the Light Intensity-Time Profile for Detection of HRP with Compounds 5a–j, and Two Other Acridans. In separate experiments, 40 µL volumes of each of three formulations were reacted with 1 µL of a solution containing $1.4\times10^{-16}$ mol of HRP in water. The formulations consisted of: (1) 0.05 mM acridan compound 5a–j in 0.01 M tris buffer, pH 8.0, 0.4 mM urea peroxide, 0.1 mM p-phenylphenol, 0.025% TWEEN 20, 1 mM EDTA; (2) an identical formulation containing phenyl 10-methylacridan-9-carboxylate in place of acridan 5 (applicant's co-pending application Ser. No. 08/061,810) and (3) an identical formulation containing the previously reported acridan ethyl 10-methylacridan-9-thiocarboxylate (F. McCapra, Pure Appl. Chem., 24, 611–629 (1970)) in place of acridan 5. FIGS. 1–8 show the improved generation of light emission using reagents containing various acridans 5 of the present invention compared to the other acridan reagents under these conditions.

Example 13

Optimization of Formulations. A matrix optimization experiment was done using acridans 5a, 5d, and 5e (0.1 mM–0.076 mM) in solutions containing p-iodophenol (0.1–2.25 mM), urea peroxide (0.1 mM–1 mM), TWEEN 20 (0–0.6%) and 2.5% (v/v) 2-methoxyethanol in tris buffer, pH 8.0 (0.01–0.2M). Sensitivity and dynamic range were evaluated for detection of HRP in the range $1.4\times10^{-15}$ to $1.4\times10^{-19}$ mol of enzyme. An especially effective reagent consists of the acridan (0.05–0.075 mM), p-iodophenol (1.1 mM) or p-phenylphenol (0.1 mM), urea peroxide (0.4–0.6 mM), 1 mM EDTA, TWEEN 20 (0.025%) in tris buffer, pH 8.0 (0.01M). These conditions gave linear assays for HRP over the entire range of enzyme tested for each acridan compound.

Example 14

Comparison of the Sensitivity of Detection of HRP with Acridans 5a, 5d, 5e and 5j Compared to Luminol. The linearity of detection of HRP using reagent compositions of the present invention and a commercially available optimized reagent containing luminol (Amersham ECL) were compared. In separate experiments, forty µL each of a solution containing acridan 5a, 5d, 5e or 5j as described in the table and forty µL of the commercial reagent (Amersham ECL, prepared according to the manufacturer's directions) were mixed at room temperature with 1 µL aliquots of HRP containing between $1.4\times10^{-15}$ and $1.4\times10^{-19}$ mol of enzyme. FIGS. 9–12 compare the linear range of HRP amount measured using reagents containing acridans 5a, 5d, 5e or 5j respectively. Data from the reagents containing acridan 5a, 5d, 5e or 5j were measured at 15 min while data from the ECL reagent was measured at the point of maximum light intensity due to the faster rise and decay of light intensity and variation of peak time with amount of enzyme for this reagent. Reagents containing acridan 5a, 5d, 5e or 5j are capable of 100-fold greater sensitivity of detection than the ECL reagent. Measurement with the reagents containing acridan 5a, 5d, 5e or 5j could be measured at earlier times with equivalent sensitivity.

|    | Acridan    | Peroxide   | Phenol    | TWEEN 20 | Buffer              |
|----|------------|------------|-----------|----------|---------------------|
| 5a | 0.05 mM    | 0.4 mM UP  | 1.1 mM IP | 0.025%   | 0.01 M tris, pH 8.0 |
| 5d | 0.075 mM   | 0.4 mM UP  | 0.1 mM PP | 0.025%   | 0.01 M tris, pH 8.0 |
| 5e | 0.075 mM   | 0.4 mM UP  | 0.1 mM PP | 0.025%   | 0.01 M tris, pH 7.0 |
| 5j | 0.075 mM   | 0.6 mM UP  | 0.1 mM PP | 0.025%   | 0.01 M tris, pH 8.0 |

Example 15

Stability of Horseradish Peroxidase Detection Reagents Containing Acridans. The detection reagents are conveniently stored in two containers, the first comprising an aqueous buffer solution containing the peroxide, phenol enhancer, TWEEN 20 and EDTA, the second solution comprising the acridan compound 5 in a water-miscible organic solvent such as 1:1 ethanol/p-dioxane or preferably, 2-methoxyethanol or 1:1 propylene glycol/ethanol. When stored in this manner, the components are stable for several months. The final detection reagent is prepared by mixing appropriate quantities of the two solutions before use. An advantage of acridans of the present invention is their greater stability in the final detection reagent mixture. Stability is assessed by measuring the peak light intensity from an aliquot of the solution reacted with a specified amount of HRP. The peak light intensities from 41 µL of each of two detection reagents containing compound 5d or 5j (0.075 mM), p-phenylphenol (0.1 mM), urea peroxide (0.4 mM–5d, 0.6 mM–5j), TWEEN 20 (0.025%), EDTA (1 mM), 2.5% 2-methoxyethanol in 0.01M tris buffer, pH 8.0 reacted with $1.4 \times 10^{-16}$ mol of HRP at room temperature stored for 24 hours are expressed as a percentage of the value obtained before storage (% $I_{max}$) below.

| Compound | Storage Time (hr) | % $I_{max}$ |
|---|---|---|
| 5d | 24 | 99 |
| 5j | 24 | 100 |

Other experiments demonstrated that acridans 5d, 5e and 5f, also show good stability.

Example 16

Effect of pH of the Buffer. Detection reagent solutions according to the compositions of Example 13 were prepared with either 0.01M tris in the pH range 7.0–9.0 or 0.01M potassium phosphate in the pH range 6.0–6.5 and reacted with HRP. The best ratio of signal to reagent background resulted from reagents with a pH in the range 6–8.5.

Example 17

Effect of Buffer Salt. Detection reagent solutions according to the compositions of Example 13 are prepared with substitution of various buffer solutions and reacted with HRP. Useful levels of light intensity compared to reagent background are obtained with reagents prepared from tris hydrochloride, tris acetate, tris malate, potassium phosphate, diglycine-sodium hydroxide and tricine buffers.

Example 18

Effect of Enhancers. Detection reagent solutions according to the compositions of Example 13 were prepared with substitution of various phenolic enhancers and reacted with HRP. Useful levels of light intensity compared to reagent background were obtained with reagents incorporating p-iodophenol, p-hydroxycinnamic acid and p-phenylphenol.

Example 19

Effect of Peroxide. Detection reagent solutions according to the compositions of Example 13 were prepared with substitution of various peroxides and reacted with HRP. Useful levels of light intensity compared to reagent background were obtained with reagents incorporating hydrogen peroxide, sodium perborate and urea peroxide.

Example 20

Effect of Surfactant. Detection reagent solutions according to the compositions of Example 13 are prepared with substitution of various surfactants and reacted with HRP. Useful levels of light intensity compared to reagent background are obtained with reagents incorporating TWEEN 20 (Aldrich, Milwaukee, Wis.), TRITON X-405 (Aldrich), BRIJ 35 (Aldrich), sodium dodecyl sulfate, cetyltrimethylammonium bromide, β-cyclodextrin and dextran sulfate.

Example 21

Improved Chemiluminescent Detection of Proteins by Western Blot. Rabbit anti-goat IgG-peroxidase conjugate was obtained from Cappel Products (Durham, N.C.). Human transferrin and fractionated goat anti-human transferrin serum were purchased from Sigma Chemical Co. (St. Louis, Mo.). The IgG sample was centrifuged at 10,000 g for two minutes and the supernatant was used in the immunological reaction. PVDF transfer membrane (IMMOBILON P) was obtained from Millipore Corp. (Bedford, Mass.). Kodak (Rochester, N.Y.) X-OMAT AR film was used in the assay procedure.

SDS-PAGE was performed utilizing the buffer system described by Laemmli (U. K. Laemmli, Nature (London), 227, 680 (1970)). The stacking gel was 4.38% acrylamide: 0.12% bisacrylamide. The separating gel was 6.81% acrylamide: 0.19% bisacrylamide. Following electrophoresis the gel was equilibrated for 7–8 minutes with the transfer buffer which contained 20 mM Tris, 153 mM glycine and 20% (v/v) methanol. The gel, sandwiched between a sheet of transfer membrane and a sheet of chromatography paper 3MM (Whatman), was placed in the transfer unit (Bio-Rad Laboratories, Richmond, Calif.). The proteins in the gel were electroeluted for 25 min at 4° C. at a 100 V constant voltage. The membrane was then placed in 50 mM Tris-HCl buffered saline at pH 7.4 (TBS) at 4° C. overnight. After this period the membrane was washed with TBS for 15 min.

The membrane was treated with 0.05% TWEEN-20 in 50 mM Tris-HCl buffered saline at pH 7.4 (T-TBS) containing 1% non-fat powdered milk (NFM) for one hour at room temperature. This blocked membrane was incubated for 75 minutes at room temperature with primary antibody (1:1500 dilution of goat anti-human transferrin IgG fraction) using T-TBS containing 1% NFM.

The membrane was then rinsed and washed three times for five min each with T-TBS at room temperature. The washed membrane was incubated for one hour at room temperature with secondary antibody (1:50,000 dilution of rabbit anti-goat IgG peroxidase conjugate) using T-TBS containing 1% NFM. The membrane was rinsed and washed four times for ten minutes each with T-TBS followed by a five min wash with TBS.

The washed membrane was soaked in one of four detection reagents for 5 min, drained and placed between sheets of transparency film. Reagent A was a commercial reagent containing luminol (Amersham ECL). Reagent B contained the acridan 4'-hydroxyphenyl 10-methylacridan-9-carboxylate previously disclosed in applicant's co-pending application Ser. No. 08/061,810. Reagent C contained acridan 5a. After an incubation period of 15 min, the X-ray film was exposed to the membrane for varying periods of time and developed. The composition of detection reagent solution containing the acridan compounds was:

| | |
|---|---|
| Tris buffer, pH 8.8 | 0.1 M |
| Acridan | 0.05 mM |
| p-iodophenol | 1.1 mM |
| TWEEN 20 | 0.5% (w/w) |
| $NaBO_3 \cdot 4H_2O$ | 2.5 mM |
| EDTA | 0.5 mM |
| p-Dioxane | 1.25% |
| Ethanol | 1.25% |

The transferrin standards utilized were clearly visible down to 5 pg/slot over the background after a 5 s exposure to Kodak X-OMAT AR X-ray film. It was possible to make several exposures of the membrane during a period of 24 hours as the membrane continued to emit light. FIG. 13 is a digitally scanned image of the X-ray film record of an experiment using a 14 min incubation and 15 s exposure. The results show the superior image obtained with acridan 5a of the present invention.

Example 22

Chemiluminescent Detection of Southern Blots. Mouse genomic DNA (Clontech Laboratories. Inc., Palo Alto, Calif.) was cleaved to completion with restriction endonuclease EcoR1 (Boehringer-Mannheim) at a concentration of 50 μg/mL. The restricted DNA was purified by extraction once with phenol/chloroform, once with chloroform and was precipitated with ethanol. The purified DNA was divided into two portions containing 34 and 17 μg of DNA, respectively and separated by 0.77% agarose gel electrophoresis. The electrophoresis buffer was 40 mM Tris-acetate and 2 mM EDTA (pH 8.0). After electrophoresis the gel was rinsed with H$_2$O and then soaked in 0.25N HCl for 12 min with gentle agitation.

MagnaGraph nylon (Micron Separations Inc., Westboro, Mass.) was soaked sequentially in water and 10×SSC (20× SSC is 3M NaCl, 0.3M sodium citrate, pH 7.0) for 2 and 10 min, respectively. The gel was rinsed with water and then treated with 0.5M NaOH/1.5M NaCl twice for 15 and 30 minutes, respectively. The gel was rinsed with water and then treated with 1M Tris-HCl (pH 7.5)/1.5M NaCl three times for 15 min each. The DNA in the gel was transferred onto the membrane by capillary blotting overnight using 10X SSC. The blots were air-dried for 30 min followed by baking at 80° C. for 2 hours.

The membranes were prehybridized in hybridization buffer (Amersham #RPN. 3000) containing 0.5N NaCl and 5% blocking agent (Amersham #RPN. 3000) for 60 min at 42° C. with occasional agitation. The hybridization probe, v-mos DNA (Clontech Lab. Inc.) was labeled with HRP according to the manufacturer's instructions (Amersham #RPN. 3000) and the hybridization proceeded overnight at 42° C. using a hybridization buffer containing 0.5N NaCl and 5% blocking agent and 300 ng/mL HRP-labeled v-mos DNA. The membranes were washed sequentially with room temperature 0.5×SSC/0.4% SDS for 5 and 30 min, then again at 55° C. three times for 15 min each, followed by two washes with 2×SSC for 5 min each at room temperature.

The membranes were rinsed with water and placed on 3 MM blotting paper for one minute to remove excess solution, then transferred to a clean container followed by the addition of the detection reagent of example 21 containing acridan 5a of the present invention. After a nine minute incubation, excess solution was drained off and the blots were placed between sheets of transparency film followed by exposure to Kodak X-OMAT XAR 5 film.

Figure 14:
Figure 2:
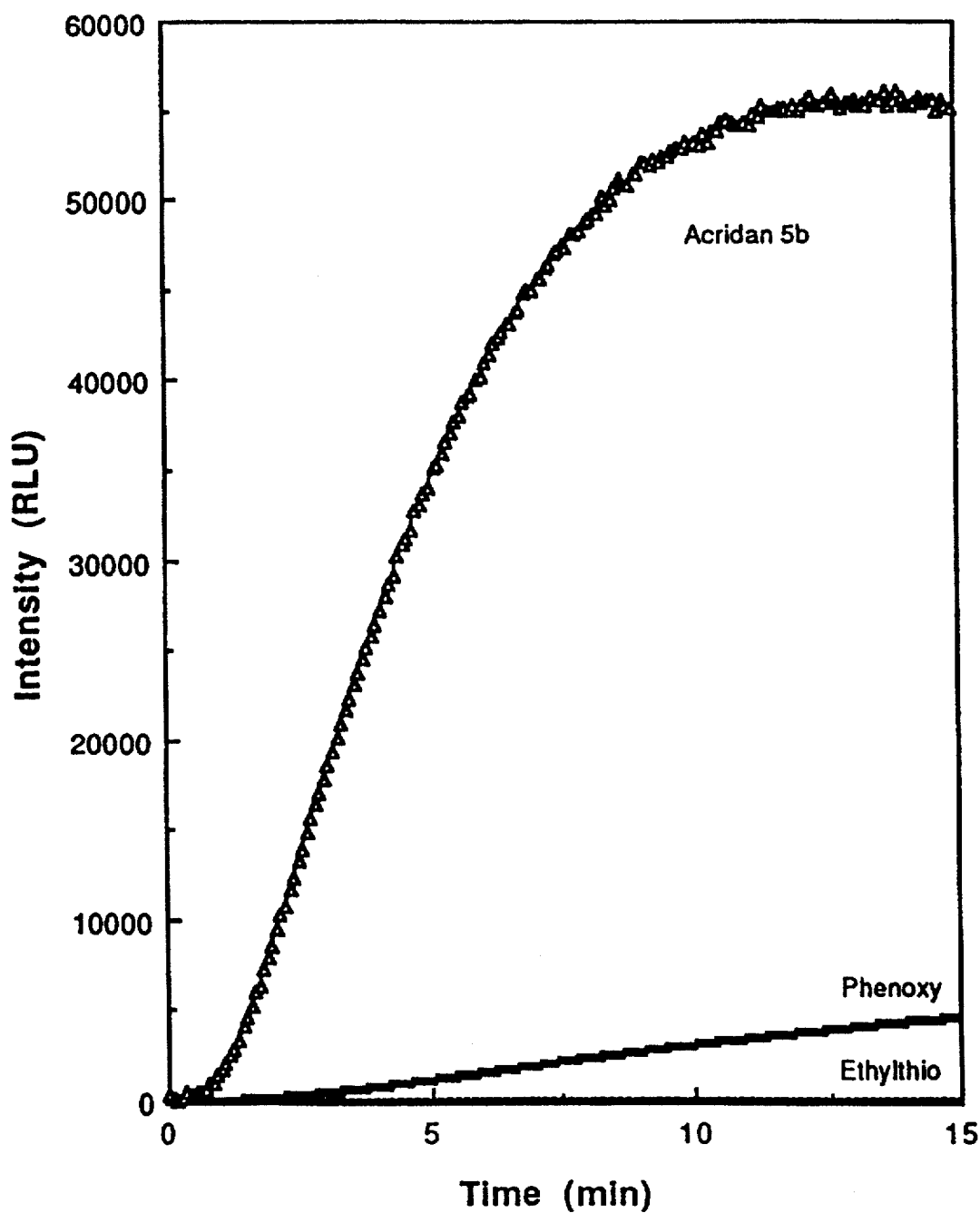
Figure 3:
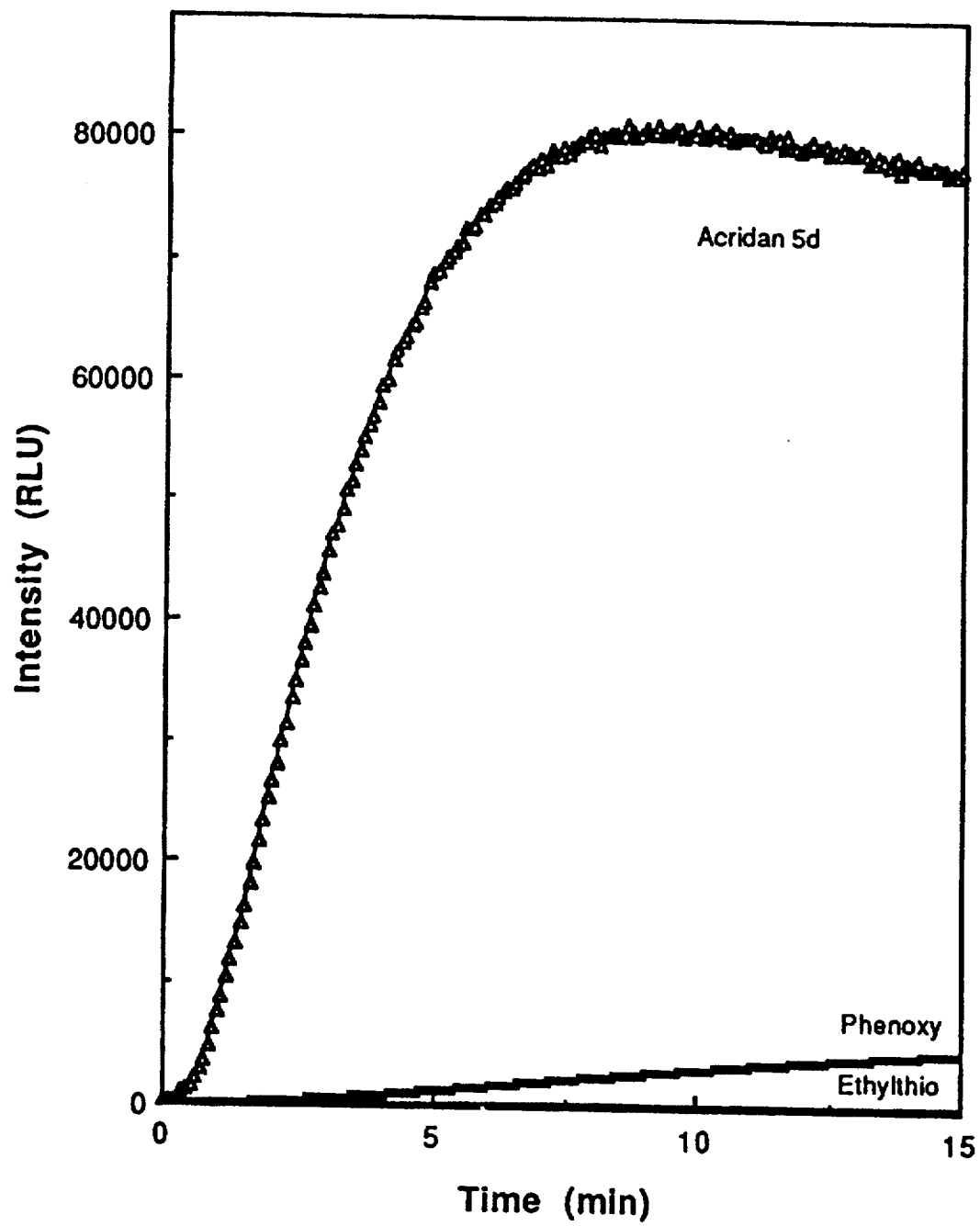
Figure 4:
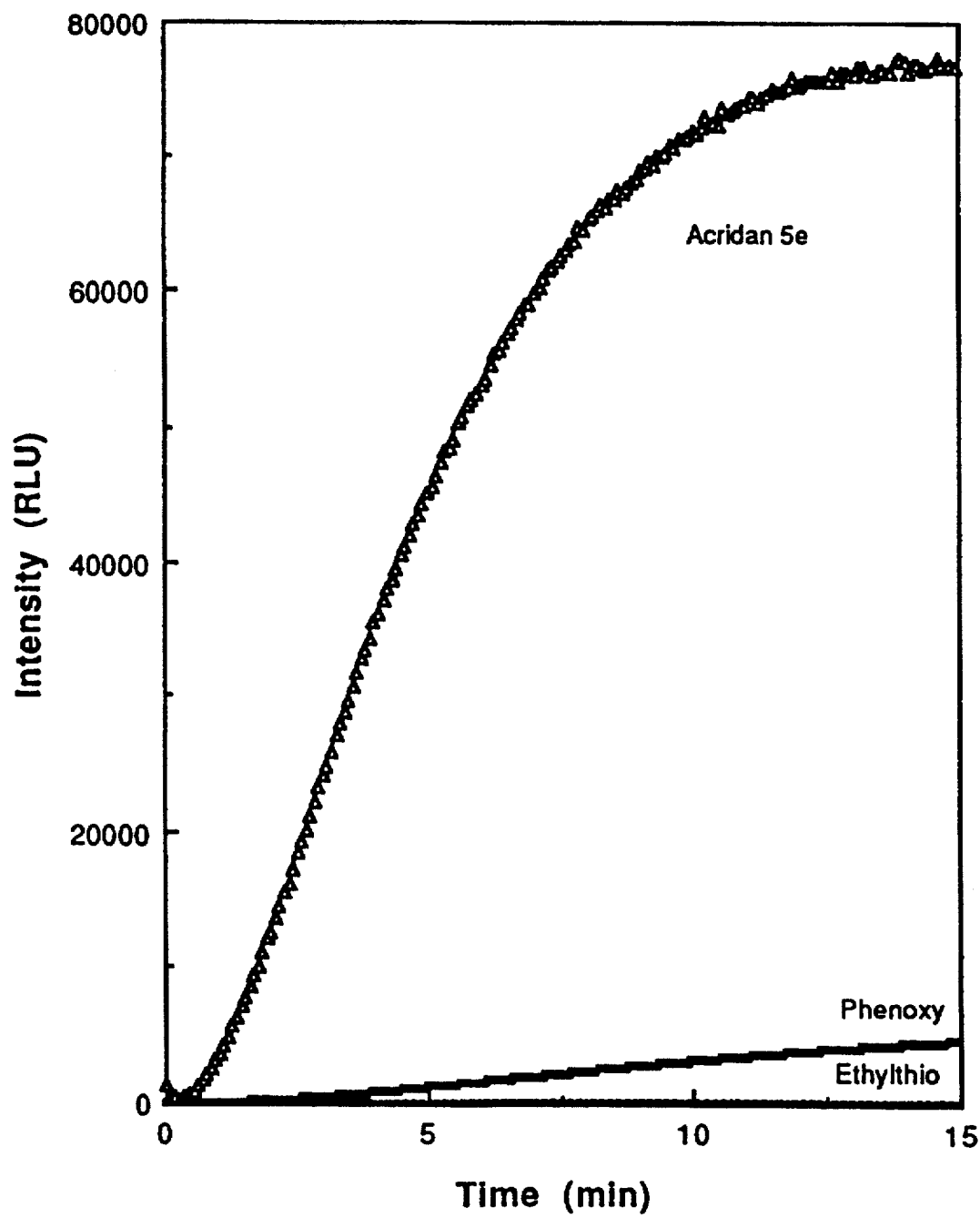
Figure 5:
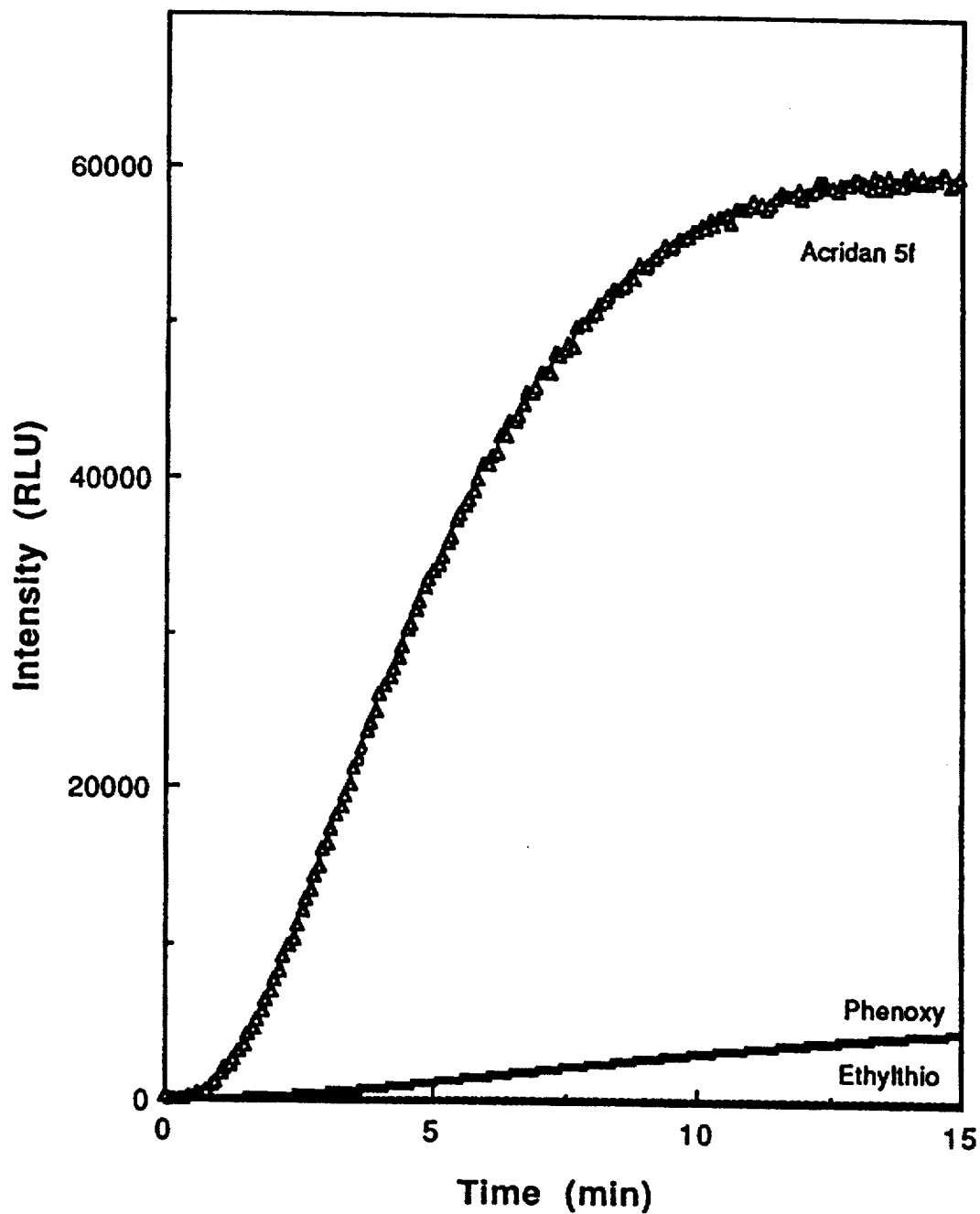
Figure 6:
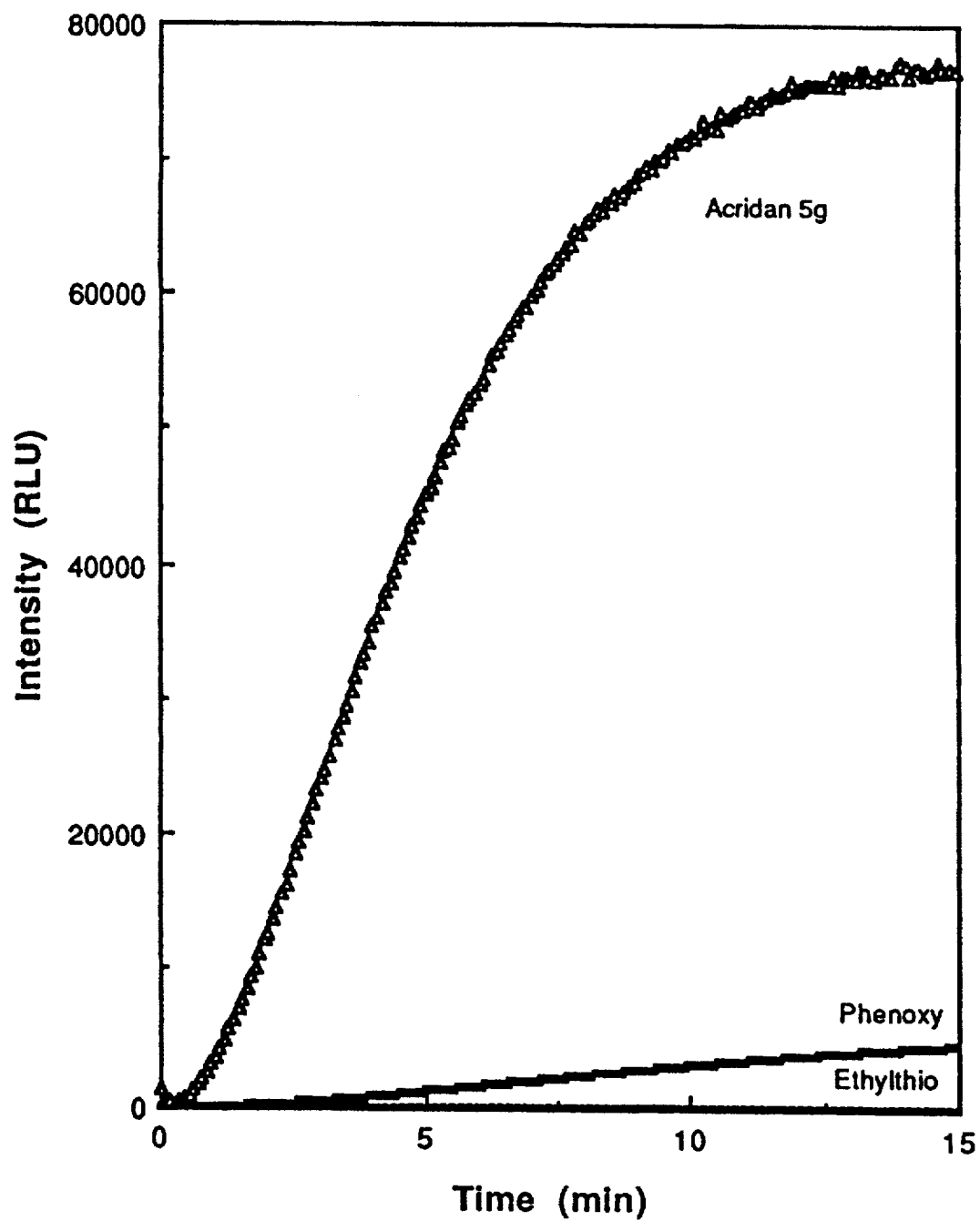
Figure 7:
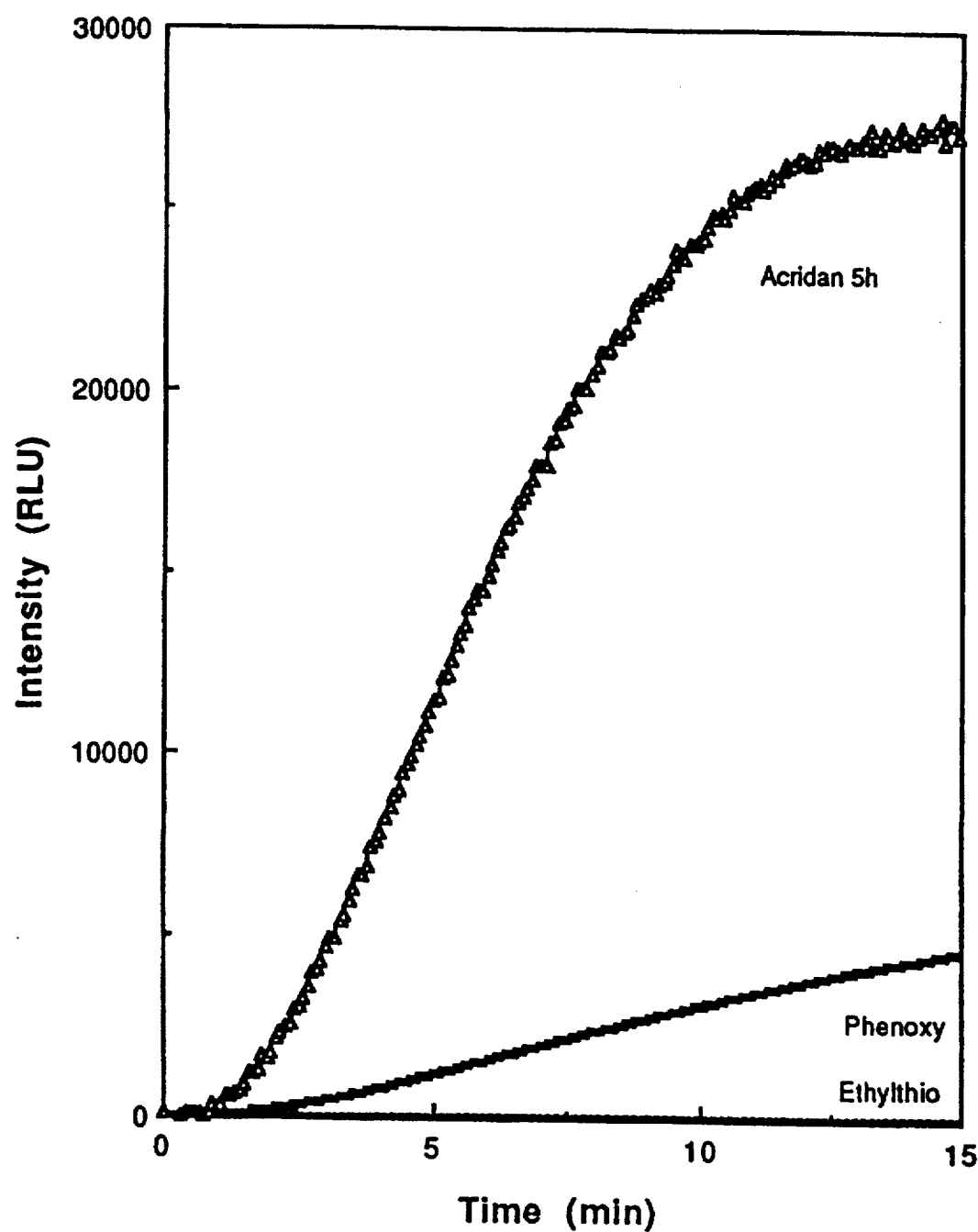
Figure 8:
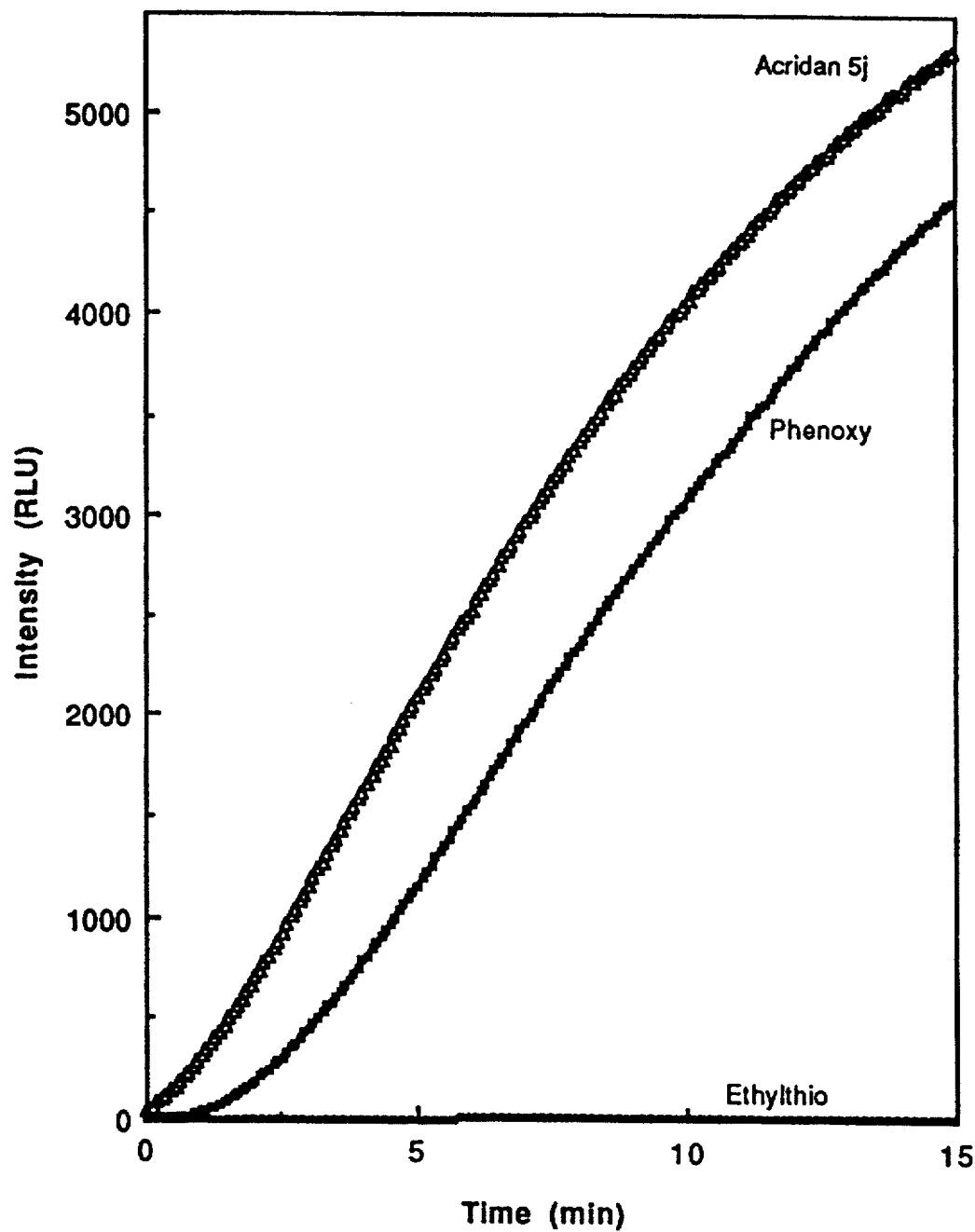
Figure 9:
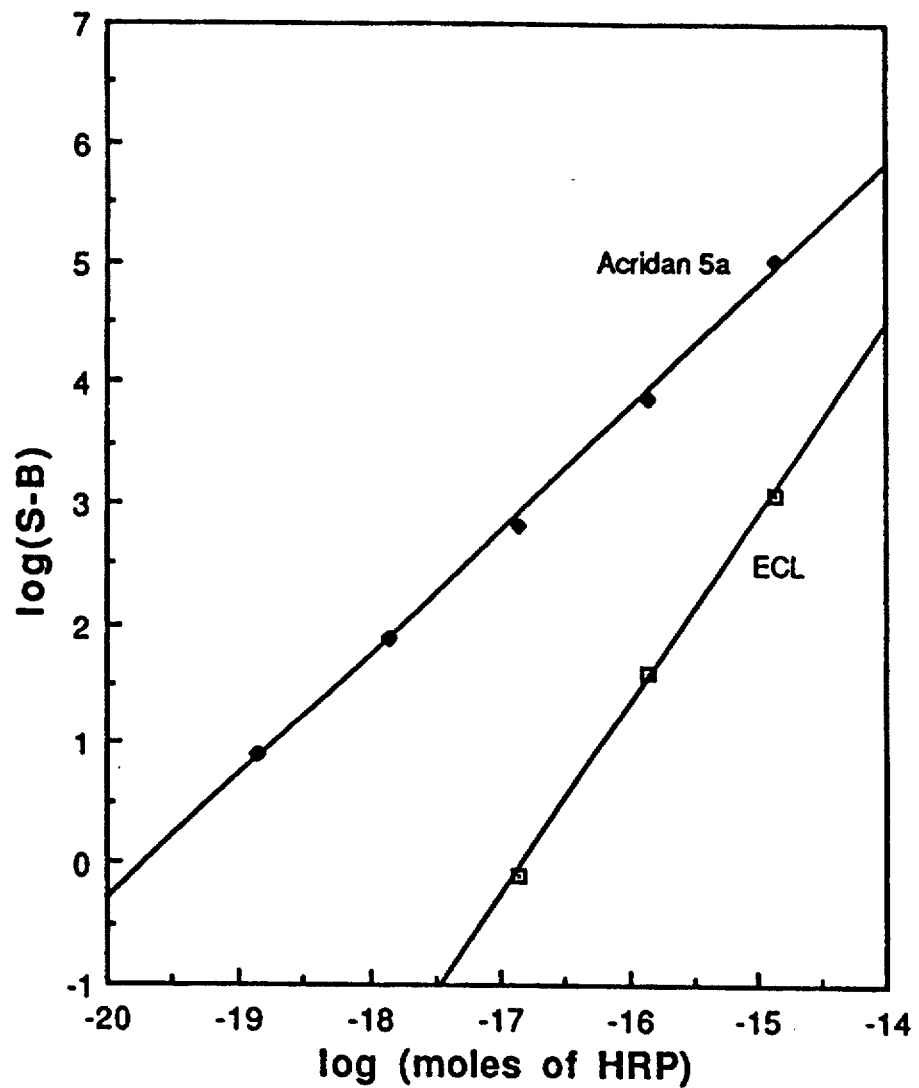
Figure 10:
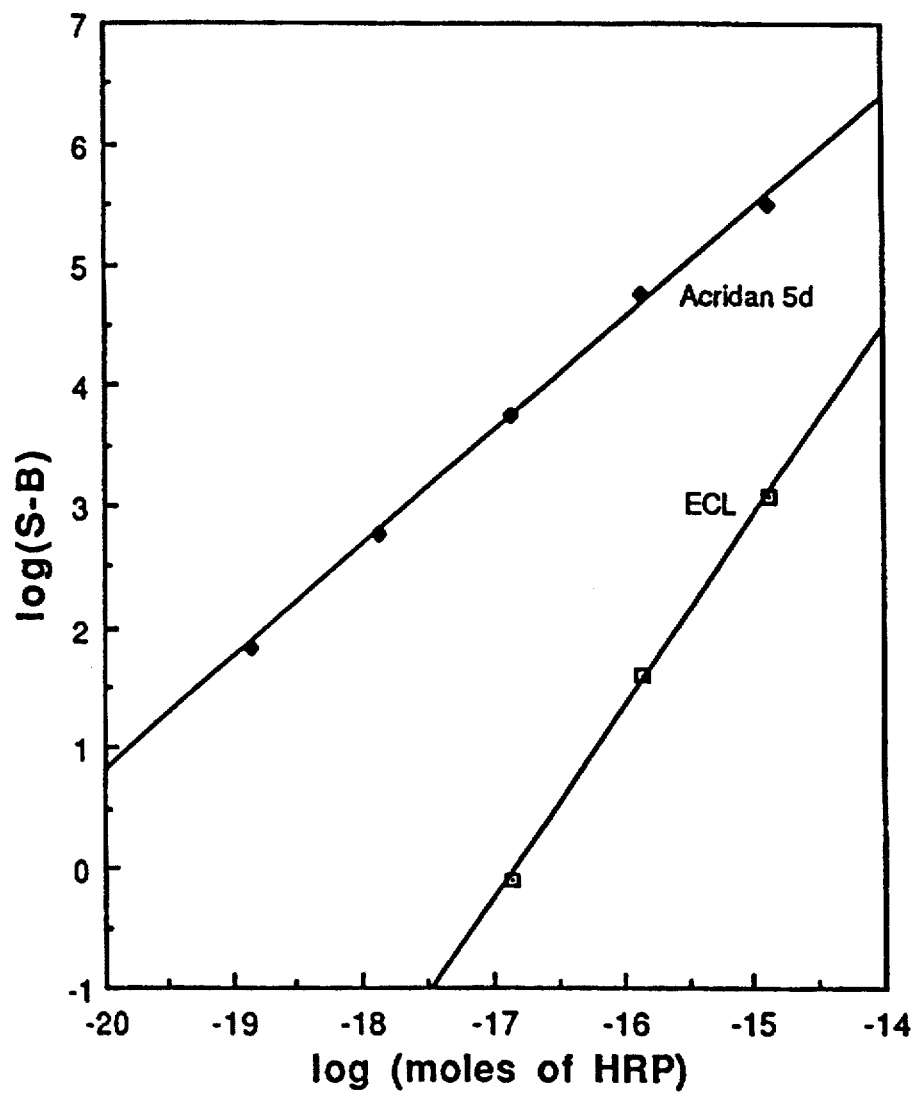
Figure 11:
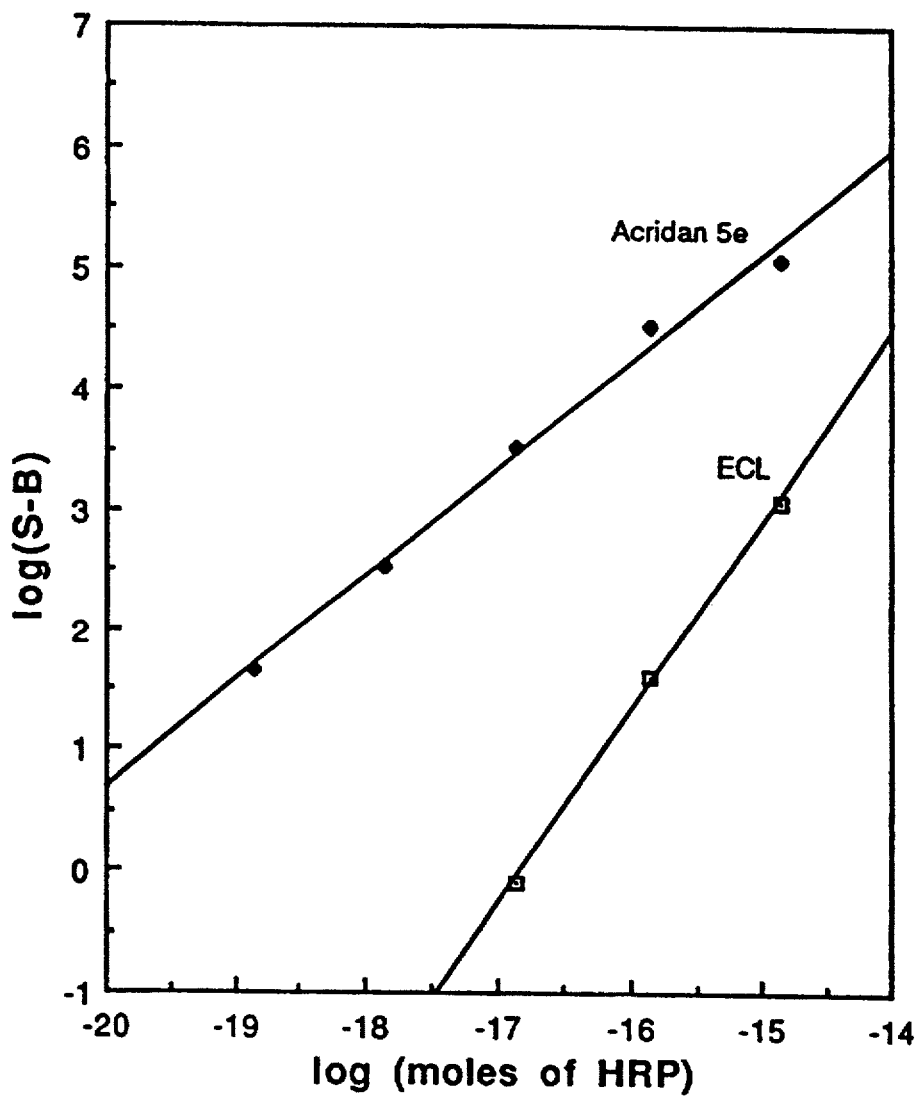
Figure 12:
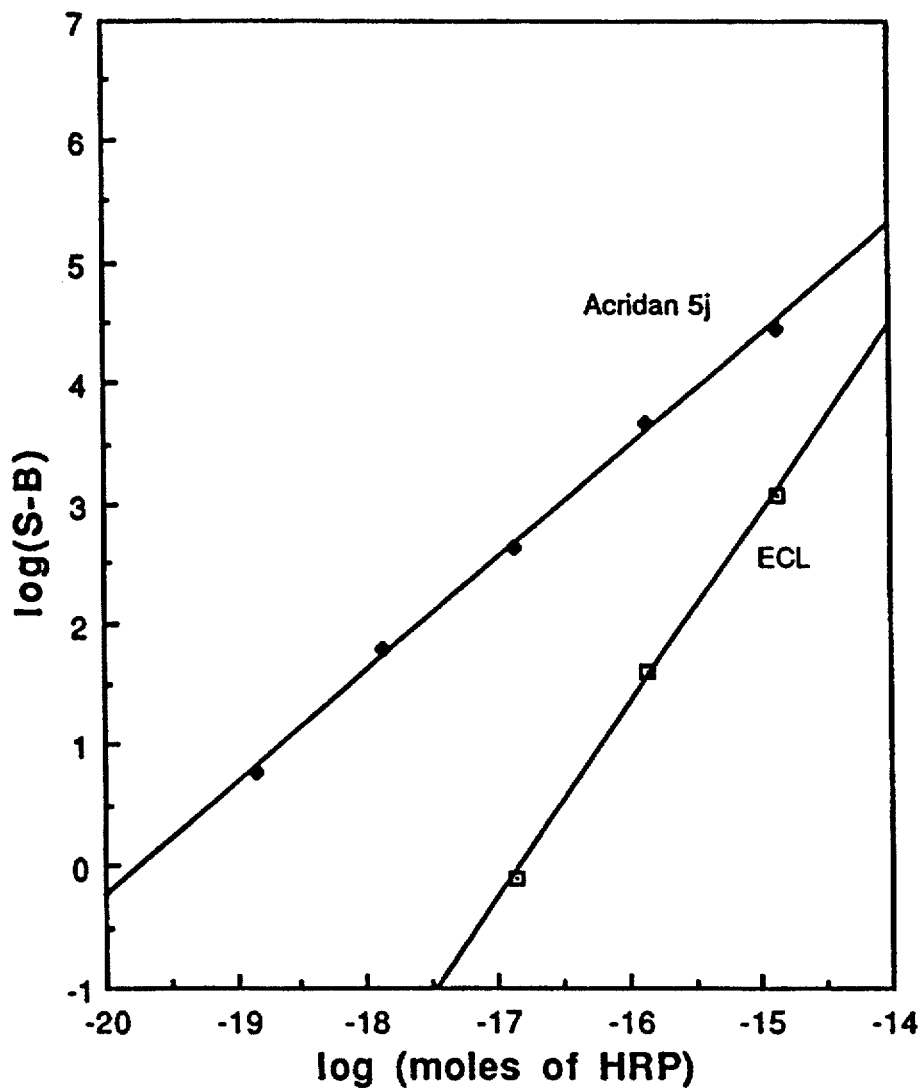
Figure 13A:
Figure 13B:
Figure 13C:
Figure 14:

The reagent of the present invention can be used to detect a single copy gene in mouse genomic DNA with exposure of only 10 min as shown in FIG. 14. The target restriction fragment is 14 kb providing 79 pg (7.9×10$^{-14}$ moles) of target DNA in the 17 μg leading tracks. The single copy gene was clearly visible in both tracks of the blot using the detection reagent of the present invention.

It is intended that the foregoing description be only illustrative of the present invention and that the present invention be limited only by the appended claims.

We claim:

1. An acridan of the formula

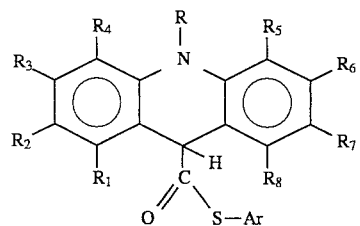

wherein R is selected from the group consisting of alkyl, heteroalkyl and aralkyl groups, wherein $R_1$ through $R_8$ are independently selected from the group consisting of hydrogen and groups which do not interfere with the production of light and wherein Ar is selected from the group consisting of substituted and unsubstituted aryl groups do not interfere with the production of light from the acridan by reaction with a peroxide and a peroxidase.

2. The acridan of claim 1 wherein Ar is an unsubstituted aryl group.

3. The acridan of claim 2 wherein the unsubstituted aryl group is selected from phenyl and naphthyl groups.

4. The acridan of claim 1 wherein Ar is a substituted aryl group.

5. The acridan of claim 4 wherein the substituted aryl group is selected from substituted phenyl and naphthyl groups.

6. The acridan of any of claim 1–5 wherein at least one of $R_1$ through $R_8$ is an alkoxy group and the remaining of $R_1$ through $R_8$ are hydrogen.

7. The acridan of any of claims 1–5 wherein at least one of $R_1$ through $R_8$ is a methoxy group and the remaining of $R_1$ through $R_8$ are hydrogen.

8. A reagent composition which generates light in the presence of a peroxidase comprising a) an acridan of the formula:

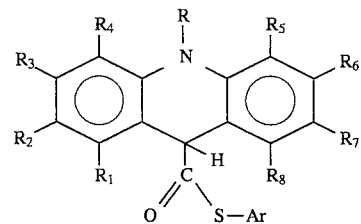

wherein R is selected from the group consisting of alkyl, heteroalkyl and aralkyl groups, wherein $R_1$ through $R_8$ are independently selected from the group consisting of hydrogen and groups which do not interfere with the production of light and wherein Ar is selected from the group consisting of substituted and unsubstituted aryl groups which do not interfere with the production of light from the acridan by reaction with a peroxide and a peroxidase;

b) optionally a phenolic compound which enhances light production;

c) the peroxide which participates in the reaction of the acridan with the peroxidase;

d) a chelating agent which prevents the peroxide compound from reacting prior to addition of the peroxidase to the composition; and e) a surfactant in an amount which provides improved chemiluminescence by reducing background.

9. The composition of claim 8 wherein Ar is an unsubstituted aryl group.

10. The composition of claim 9 wherein the unsubstituted aryl group is selected from the group consisting of phenyl and naphthyl groups.

11. The composition of claim 8 wherein Ar is a substituted aryl group.

12. The composition of claim 11 wherein the substituted aryl group is selected from the group consisting of substituted phenyl and naphthyl groups.

13. The composition of any one of claims 8, 9, 10, 11 or 12 wherein at least one of $R_1$ through $R_8$ is an alkoxy group and the remaining of $R_1$ through $R_8$ are hydrogen.

14. The composition of any one of claims 8, 9, 10, 11 or 12 wherein at least one of $R_1$ through $R_8$ is a methoxy group and the remaining the $R_1$ through $R_8$ are hydrogen.

15. A method for producing chemiluminescence comprising reacting a peroxide compound and a peroxidase with an acridan of the formula

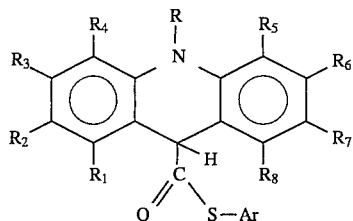

wherein R is selected from the groups consisting of alkyl, heteroalkyl and aralkyl groups, wherein $R_1$ through $R_8$ are independently selected from the group consisting the hydrogen and groups which do not interfere with the production of light and wherein Ar is selected from the group consisting of substituted and unsubstituted aryl groups which do not interfere with the production of light from the acridan by reaction with the peroxide and the peroxidase.

16. The method of claim 15 wherein Ar is an unsubstituted aryl group.

17. The method of claim 16 wherein the unsubstituted aryl group is selected from the group consisting of phenyl and naphthyl groups.

18. The method of claim 15 wherein Ar is a substituted aryl group.

19. The method of claim 18 wherein the substituted aryl group is selected from the group consisting of the substituted phenyl and naphthyl groups.

20. The method of any one of claims 15, 16, 17, 18 or 19 wherein at least one of $R_1$ through $R_8$ is an alkoxy group and the remaining of $R_1$ through $R_8$ are hydrogen.

21. The method of any one of claims 15, 16, 17, 18 or 19 wherein at least one of $R_1$ through $R_8$ is a methoxy group and the remaining of $R_1$ through $R_8$ are hydrogen.

22. A method of detecting an analyte selected from the group consisting of hydrogen peroxide, hydrogen peroxide generated by an enzyme, peroxidase alone, organic molecules labeled with the peroxidase and biological molecules labeled with the peroxidase in an assay procedure by a chemiluminescent reaction comprising reacting an acridan in the presence of a sample suspected of containing an analyte with a peroxide and the peroxidase to produce light for detecting the analyte, wherein the acridan is the formula:

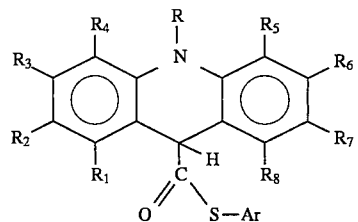

wherein R is selected from the group consisting of a alkyl, heteroalkyl and aralkyl groups, wherein $R_1$ through $R_8$ are independently selected from the group consisting of hydrogen and groups which do not interfere with the production of light and wherein Ar is selected from the group consisting of substituted and unsubstituted aryl groups which do not interfere with the production of light from the acridan to detect the analyte by reaction with the peroxide and the peroxidase.

23. The method of claim 22 wherein Ar is an unsubstituted aryl group.

24. The method of claim 23 wherein the unsubstituted aryl group is selected from the group consisting of phenyl and naphthyl groups.

25. The method of claim 22 wherein Ar is a substituted aryl group.

26. The method of claim 25 wherein the substituted aryl group is selected from the group consisting of substituted phenyl and naphthyl groups.

27. The method of any one claims 22, 23, 24, 25 or 26 wherein at least one of $R_1$ through $R_8$ is an alkoxy group and the remaining of $R_1$ through $R_8$ are hydrogen.

28. The method of any one of claims 22, 23, 24, 25 or 26 wherein at least one of $R_1$ through $R_8$ is a methoxy group and the remaining of $R_1$ through $R_8$ are hydrogen.

29. The method of claim 22 wherein the analyte is the peroxidase.

30. The method of claim 22 wherein the analyte is the peroxide.

31. A method of detecting an analyte selected from the group consisting of peroxidase alone, organic molecules labeled with the peroxidase and biological molecules labeled with the peroxidase in an assay procedure by a chemiluminescent reaction comprising:

a) providing a reagent composition which generates light in the presence of a peroxidase which comprises an acridan of the formula:

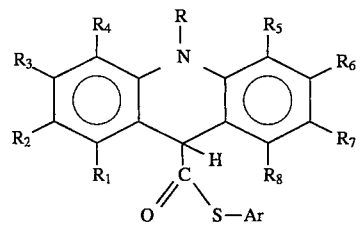

wherein R is selected from the group consisting of alkyl, heteroalkyl and aralkyl groups, wherein $R_1$ through $R_8$ are independently selected from the group consisting of hydrogen and groups which do not interfere with the production of light and wherein Ar is selected from the group consisting of substituted and unsubstituted aryl groups which do not interfere with the production of light from the acridan by reaction with a peroxide and a peroxidase; optionally a phenolic compound which enhances light production from the acridan; the peroxide which participates in the reaction of the acridan with the peroxidase; a chelating agent which prevents the peroxide from reacting prior to addition of the peroxidase to the composition; and a surfactant in an amount which provides improved chemiluminescene by reducing background; and b) reacting the peroxidase with the reagent composition so that light is produced to detect the analyte.

32. The method of claim 31 wherein Ar is an unsubstituted aryl group.

33. The method of claim 32 wherein the unsubstituted aryl group is selected from the group consisting of phenyl and naphthyl groups.

34. The method of claim 31 wherein Ar is a substituted aryl group.

35. The method of claim 34 wherein the substituted aryl group is selected from the group consisting of substituted phenyl and naphthyl groups.

36. The method of any one of claims 31, 32, 33, 34 or 35 wherein at least one of $R_1$ through $R_8$ is an alkoxy group and the remaining of $R_1$ through $R_8$ are hydrogen.

37. The method of any one of claims 31, 32, 33, 34 or 35 wherein at least one or $R_1$ through $R_8$ is a methoxy group and the remaining of $R_1$ through $R_8$ are hydrogen.

38. The method of claim 31 wherein the analyte is the peroxidase.

39. The method of claim 31 wherein the analyte is the peroxide.

40. A kit for detecting an analyte selected from the group consisting of hydrogen peroxide, hydrogen peroxide generated by an enzyme, peroxidase alone, organic molecules labeled with the peroxidase and biological molecules labeled with the peroxidase in an assay procedure by a chemiluminescent reaction comprising in separate containers:

a) an acridan of the formula:

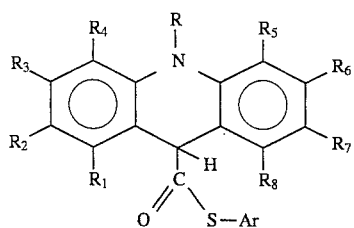

wherein R is selected from the group consisting of alkyl, heteroalkyl and aralkyl groups, wherein $R_1$ through $R_8$ are independently selected from the group consisting of hydrogen and groups which do not interfere with the production of light and wherein Ar is selected from the group consisting of substituted and unsubstituted aryl groups which do not interfere with the production of light from the acridan by reaction with a peroxide and the peroxidase;

b) the peroxide and c) the peroxidase and enzyme either singly or attached to an analyte-binding compound, wherein the light is detected in the assay procedure by reacting the acridan compound with the peroxide and the peroxidase enzyme to detect the analyte.

41. The kit of claim 40 wherein Ar is an unsubstituted aryl group.

42. The kit of claim 41 wherein the unsubstituted aryl group is selected from the group consisting of phenyl and naphthyl groups.

43. The kit of claim 40 wherein Ar is a substituted aryl group.

44. The kit of claim 43 wherein the substituted aryl group is selected from the group consisting of substituted phenyl and naphthyl groups.

45. The kit of any one of claims 40, 41, 42, 43 or 44 wherein at least one or $R_1$ through $R_8$ is an alkoxy group and the remaining of $R_1$ through $R_8$ are hydrogen.

46. The kit of any one of claims 40, 41, 42 43 or 44 wherein at least one of $R_1$ through $R_8$ is a methoxy group and the remaining of $R_1$ through $R_8$ are hydrogen.

47. The kit for detecting an analyte selected from the group consisting of peroxidase alone, organic molecules labeled with the peroxidase and biological molecules labeled with the peroxidase in an assay procedure by a chemiluminescent reaction comprising providing in separate containers:

a) a reagent composition which generates light in the presence of the peroxidase which comprises an acridan of the formula:

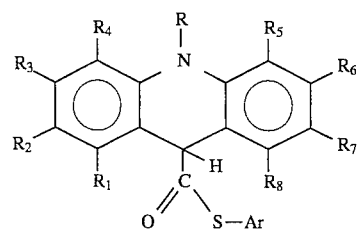

wherein R is selected from the group consisting of alkyl, heteroalkyl and aralkyl groups, wherein $R_1$ through $R_8$ are independently selected from the group consisting of hydrogen and groups which do not interfere with the production of light and wherein Ar selected from the group consisting of substituted and unsubstituted aryl groups which do not interfere with the production of light from the acridan by reaction with a peroxide an the peroxidase; optionally a phenolic compound which enhances light production from the acridan; the peroxide which participates in the reaction of the acridan with the peroxidase; a chelating agent which prevents the peroxide compound from reacting prior to addition of the peroxidase to the composition; and a surfactant in an amount which provides improved chemiluminescene which reduces background; and b) the peroxidase enzyme either singly or attached to an analyte-binding compound, wherein the light is detected in the assay procedure by reacting the reagent composition with the peroxidase enzyme to detect the analyte.

48. The kit of claim 47 wherein Ar is the unsubstituted aryl group.

49. The kit of claim 48 wherein the unsubstituted aryl group is selected from the group consisting of phenyl and naphthyl groups.

50. The kit of claim 47 wherein Ar is a substituted aryl group.

51. The kit of claim 50 wherein the substituted aryl group is selected from the group consisting of substituted phenyl and naphthyl groups.

52. The kit of any one of claims 47, 48, 49, 50 or 51 wherein at least one of $R_1$ through $R_8$ is an alkoxy group and the remaining of $R_1$ through $R_8$ are hydrogen.

53. The kit of any one claims 47, 48, 49, 50 or 51 wherein at least one of $R_1$ through $R_8$ is methoxy group and the remaining of $R_1$ through $R_8$ are hydrogen.

54. A compound which is phenyl 10-methylacridan-9-thiocarboxylate.

55. A compound which is 4'-hydroxyphenyl 10-methylacridan-9-thiocarboxylate.

56. A compound which is 2',6'-dimethylphenyl 10-methylacridan-9-thiocarboxylate.

57. A compound which is 4'-fluorophenyl 10-methylacridan-9-thiocarboxylate.

58. A compound which is 4'-trifluoromethylphenyl 10-methylacridan-9-thiocarboxylate.

59. A compound which is 4'-methoxyphenyl 10-methylacridan-9-thiocarboxylate.

60. A compound which is 2',6'-dichlorophenyl 10-methylacridan-9-thiocarboxylate.

61. A compound which is 2'-naphthyl 10-methylacridan-9-thiocarboxylate.

62. A compound which is 2'-naphthyl 2,7-dimethoxy-10-methylacridan-9-thiocarboxylate.

63. A compound which is 4'-fluorophenyl 3-methoxy-10-methylacridan-9-thiocarboxylate.

64. The composition of claim 8 wherein the acridan is selected from the group consisting of phenyl 10-methylacridan-9-thiocarboxylate; 4'-hydroxyphenyl 10-methylacridan-9-thiocarboxylate; 2',6'-dimethylphenyl 10-methylacridan-9-thiocarboxylate; 4'-fluorophenyl 10-methylacridan-9-thiocarboxylate; 4'-trifluoromethylphenyl 10-methylacridan-9-thiocarboxylate; 4'-methoxyphenyl 10-methylacridan-9-thiocarboxylate; 2',6'-dichlorophenyl 10-methylacridan-9-thiocarboxylate; 2'-naphthyl 10-methylacridan-9-thiocarboxylate; 2'-naphthyl 2,7-dimethoxy-10-methylacridan-9-thiocarboxylate; and 4'-fluorophenyl 3-methoxy-10-methylacridan-9-thiocarboxylate.

65. The method of any one of claims 15, 22, or 31 wherein the acridan is selected from the group consisting of phenyl 10-methylacridan-9-thiocarboxylate; 4'-hydroxyphenyl 10-methylacridan-9-thiocarboxylate; 2',6'-dimethylphenyl 10-methylacridan-9-thiocarboxylate; 4'-fluorophenyl 10-methylacridan-9-thiocarboxylate; 4'-trifluoromethylphenyl 10-methylacridan-9-thiocarboxylate; 4'-methoxyphenyl 10-methylacridan-9-thiocarboxylate; 2',6'-dichlorophenyl 10-methylacridan-9-thiocarboxylate; 2'-naphthyl 10-methylacridan-9-thiocarboxylate; 2'-naphthyl 2,7-dimethoxy-10-methylacridan-9-thiocarboxylate; and 4'-fluorophenyl 3-methoxy-10-methylacridan-9-thiocarboxylate.

66. The kit of any one of claims 40 or 47 wherein the acridan is selected from the group consisting of phenyl 10-methylacridan-9-thiocarboxylate; 4'-hydroxyphenyl 10-methylacridan-9-thiocarboxylate; 2',6'-dimethylphenyl 10-methylacridan-9-thiocarboxylate; 4'-fluorophenyl 10-methylacridan-9-thiocarboxylate; 4'-trifluoromethylphenyl 10-methylacridan-9-thiocarboxylate; 4'-methoxyphenyl 10-methylacridan-9-thiocarboxylate; 2',6'-dichlorophenyl 10-methylacridan-9-thiocarboxylate; 2'-naphthyl 10-methylacridan-9-thiocarboxylate; 2'-naphthyl 2,7-dimethoxy-10-methylacridan-9-thiocarboxylate; and 4'-fluorophenyl 3-methoxy-10-methylacridan-9-thiocarboxylate.

* * * * *

UNITED STATES PATENT AND TRADEMARK OFFICE
CERTIFICATE OF CORRECTION

PATENT NO. : 5,523,212
DATED : June 4, 1996
INVENTOR(S) : Hashem Akhavan-Tafti, et. al.

It is certified that error appears in the above-identified patent and that said Letters Patent is hereby corrected as shown below:

Drawings:

Delete Figures 8, 9, 10A and 10B and substitute therefor Figures 8, 9, 10, and 11 as shown on the attached pages.

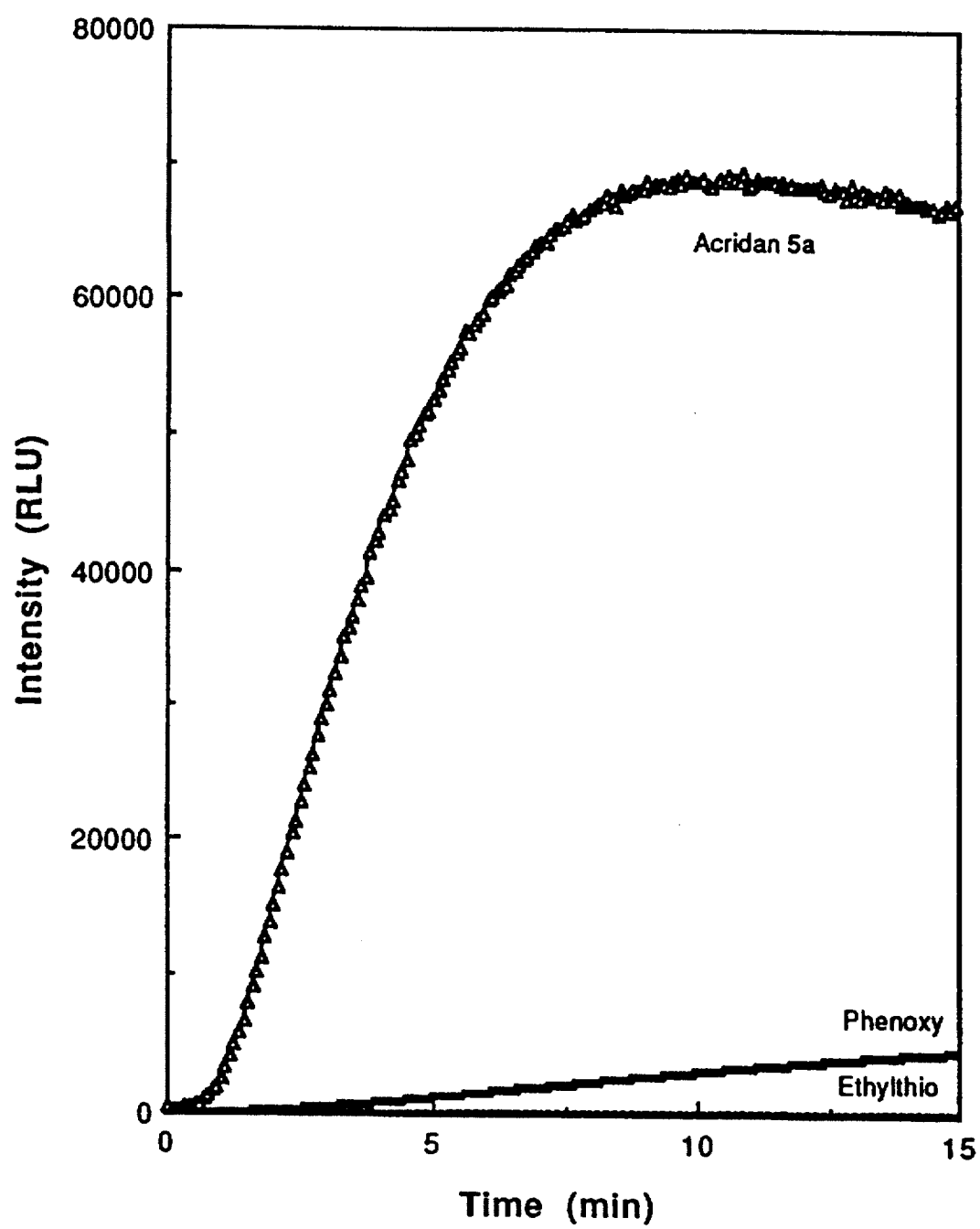

1 2 3 4 5

1 2 3 4 5

1 2 3 4 5

160  80 pg

UNITED STATES PATENT AND TRADEMARK OFFICE
CERTIFICATE OF CORRECTION

PATENT NO. : 5,523,212

DATED : June 4, 1996

INVENTOR(S) : Hashem Akhavan-Tafti, Renuka DeSilva and Zahra Arghavani

It is certified that error appears in the above—identified patent and that said Letters Patent is hereby corrected as shown below:

Column 6, line 55, "1.4 x 10-16" should be --$1.4 \times 10^{-16}$--.

Column 7, line 8, "0,025%" should be --0.025%--.

Column 8, line 11, "acridan a" should be --acridan 5a--.

Column 10, line 51, "selection" should be --selected--.

Column 12, line 53, "carboxYlate" should be --carboxylate--.

UNITED STATES PATENT AND TRADEMARK OFFICE
CERTIFICATE OF CORRECTION

PATENT NO. : 5,523,212
DATED : June 4, 1996
INVENTOR(S) : Hashem Akhavan-Tafti, Renuka DeSilva and Zahra Arghavani It is certified that error appears in the above—identified patent and that said Letters Patent is hereby corrected as shown below:

Column 14, lines 4, 11, the structure:

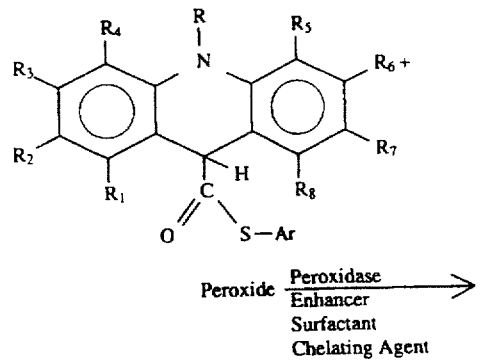

should be as follows:

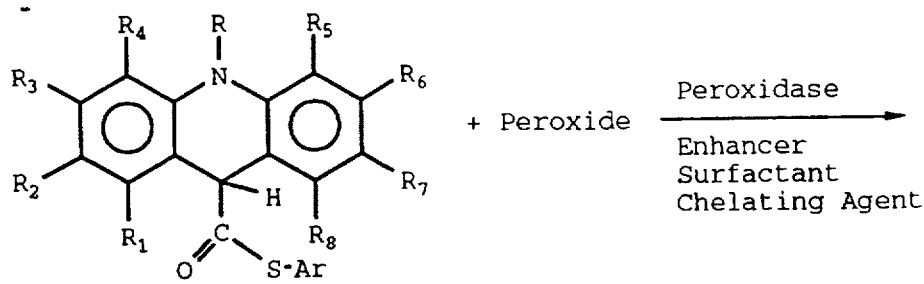

Column 16, lines 33 and 34, "1 x 10⁻$_5$" should be --1 x $10^{-5}$--.

Column 18, line 45, "compounds were " should be --compounds 1 were--.

UNITED STATES PATENT AND TRADEMARK OFFICE
CERTIFICATE OF CORRECTION

PATENT NO. : 5,523,212
DATED : June 4, 1996
INVENTOR(S) : Hashem Akhavan-Tafti, Renuka DeSilva and Zahra Arghavani It is certified that error appears in the above—identified patent and that said Letters Patent is hereby corrected as shown below:

Column 22, line 23, last line of table "0.20 f" should be --0.20 g--.

Column 23 line 59, "2.68" should be --$\delta$ 2.68--.

Column 24, line 18, "10-methylacridan-thiocarboxylate" should be --10-methylacridan-9-thiocarboxylate--.

Column 24, line 50, "5.19" should be --$\delta$ 5.19--.

Column 24, line 66, "(d, 2)" should be --(d, 2H)--.

Column 26, Table, "1.1 mM IP" should be --1.1 mM PP--.

Column 26, line 66, "(0,075 mM)" should be --(0.075 mM)--.

Column 29, line 47, "(7.9 x $10^{-J}$ moles)" should be --(7.9 x $10^{-17}$ moles)--.

Column 30, line 4 (Claim 1), after "groups" and before "do", --which-- should be inserted.

Column 30, line 67 (Claim 14), after "remaining", "the" should be deleted and --of-- inserted therefor.

Column 32, line 8 (Claim 27), after "one" and before "claims", --of-- should be inserted.

UNITED STATES PATENT AND TRADEMARK OFFICE
CERTIFICATE OF CORRECTION

PATENT NO. : 5,523,212
DATED : June 4, 1996
INVENTOR(S) : Hashem Akhavan-Tafti, Renuka DeSilva and Zahra Arghavani It is certified that error appears in the above-indentified patent and that said Letters Patent is hereby corrected as shown below:

Column 34 line 19 (Claim 47), after "peroxide", "an" should be deleted and --and-- inserted therefor.

Signed and Sealed this

Thirtieth Day of September, 1997

Attest:

BRUCE LEHMAN

Attesting Officer

Commissioner of Patents and Trademarks